(12) United States Patent
Tomasetti et al.

(10) Patent No.: US 6,256,374 B1
(45) Date of Patent: Jul. 3, 2001

(54) MINIATURE C-ARM APPARATUS WITH DUAL VIDEO DISPLAY MONITOR AND SINGLE DRIVER INTERFACE THEREFOR

(75) Inventors: Perry J. Tomasetti, Elmwood Park; Sandra L. Brown, Belvidere; William E. Higgins, Palos Heights, all of IL (US)

(73) Assignee: FluoroScan Imaging Systems, Inc., Northbrook, IL (US)

( * ) Notice: Subject to any disclaimer, the term of this patent is extended or adjusted under 35 U.S.C. 154(b) by 0 days.

(21) Appl. No.: 09/419,593

(22) Filed: Oct. 18, 1999

Related U.S. Application Data

(60) Provisional application No. 60/109,968, filed on Nov. 25, 1998, and provisional application No. 60/104,810, filed on Oct. 19, 1998.

(51) Int. Cl.[7] ........................................ H05G 1/64
(52) U.S. Cl. .................................. 378/98.2; 378/198
(58) Field of Search .................... 378/98, 98.2, 102, 378/189, 190, 193, 197, 198, 204, 62

(56) References Cited

U.S. PATENT DOCUMENTS

| | | | |
|---|---|---|---|
| 4,142,101 | 2/1979 | Yin | 250/363 R |
| 4,674,107 * | 6/1987 | Urban et al. | 378/98 |
| 5,379,334 * | 1/1995 | Zimmer et al. | 378/98.2 |
| 5,627,873 * | 5/1997 | Hanover et al. | 378/197 |
| 5,949,846 | 9/1999 | Stein et al. | 378/54 |
| 6,007,243 | 12/1999 | Ergun et al. | 378/197 |
| 6,113,265 | 9/2000 | Babler | 378/197 |

OTHER PUBLICATIONS

U.S. Patent application No. 09/270,373 filed Mar. 16, 1999, Tomasetti et al.

* cited by examiner

*Primary Examiner*—David P. Porta
(74) *Attorney, Agent, or Firm*—Cooper & Dunham LLP

(57) ABSTRACT

An x-ray fluoroscopic imaging system including a portable cabinet, a monitor having two video displays, a support arm, an articulated arm assembly connecting the support arm to the cabinet, a C-arm carried by the support arm assembly, an x-ray source and detector located at opposing locations on the C-arm, and a control panel mounted on the source or the detector, wherein the two displays are SVGA multiscan CRTs, mounted in a single rotating enclosure, which provide certain functions of the imaging system. A single driver interface is provided for the two displays for 100% synchronous operation of both displays to display images required by the fluoroscopic imaging system.

6 Claims, 22 Drawing Sheets

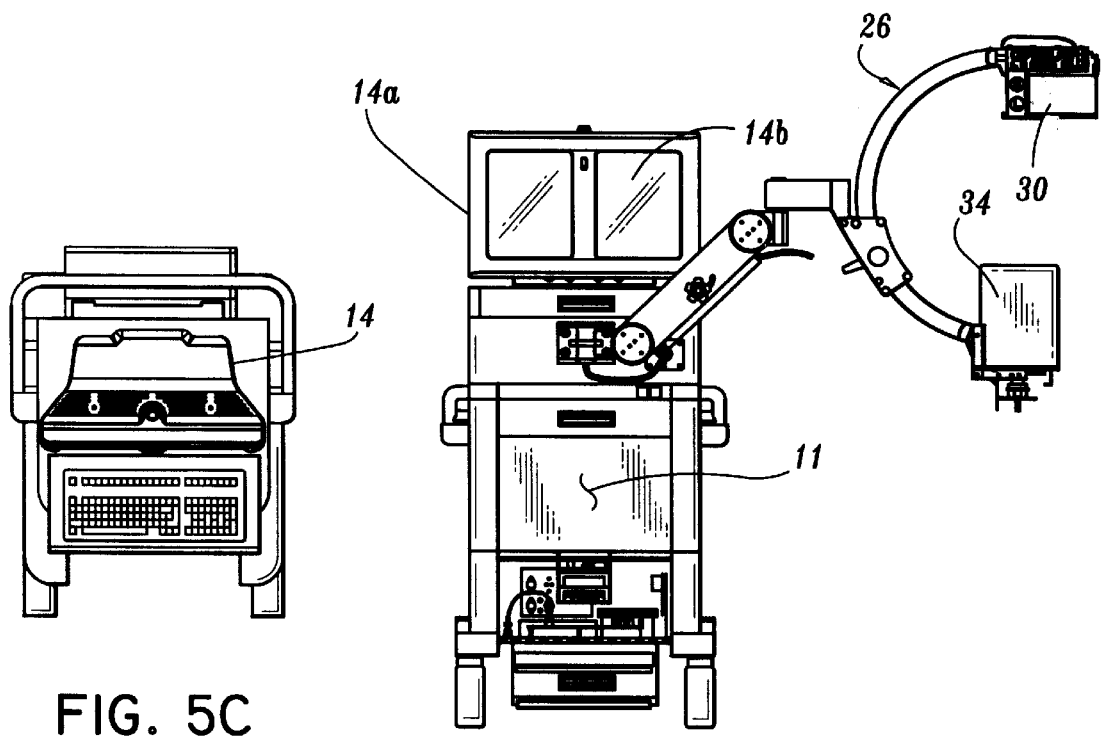
FIG. 5C
FIG. 5B
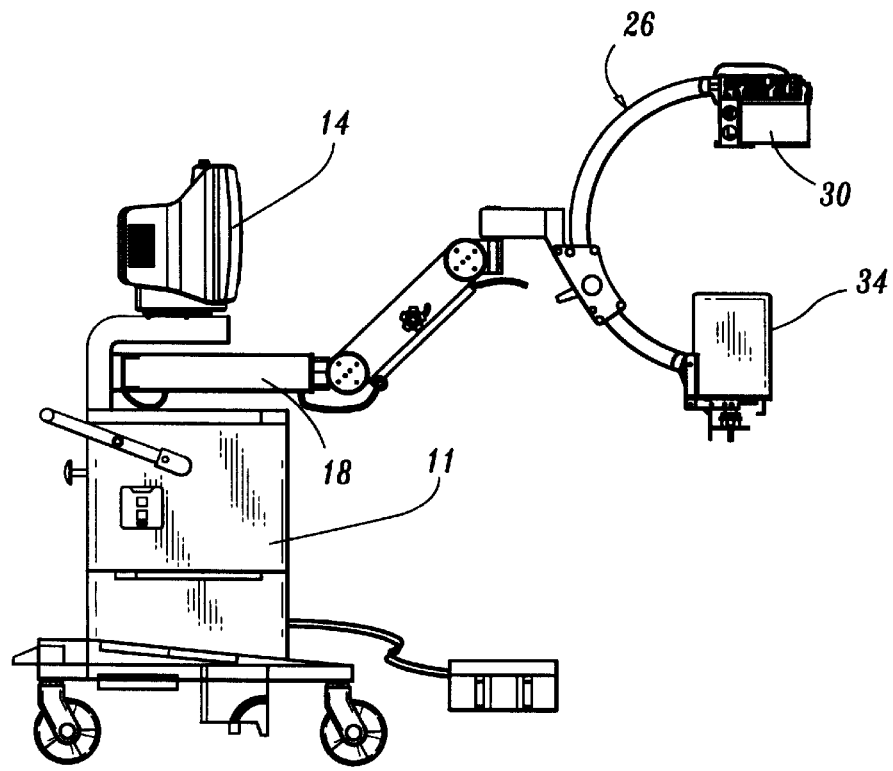
FIG. 5A

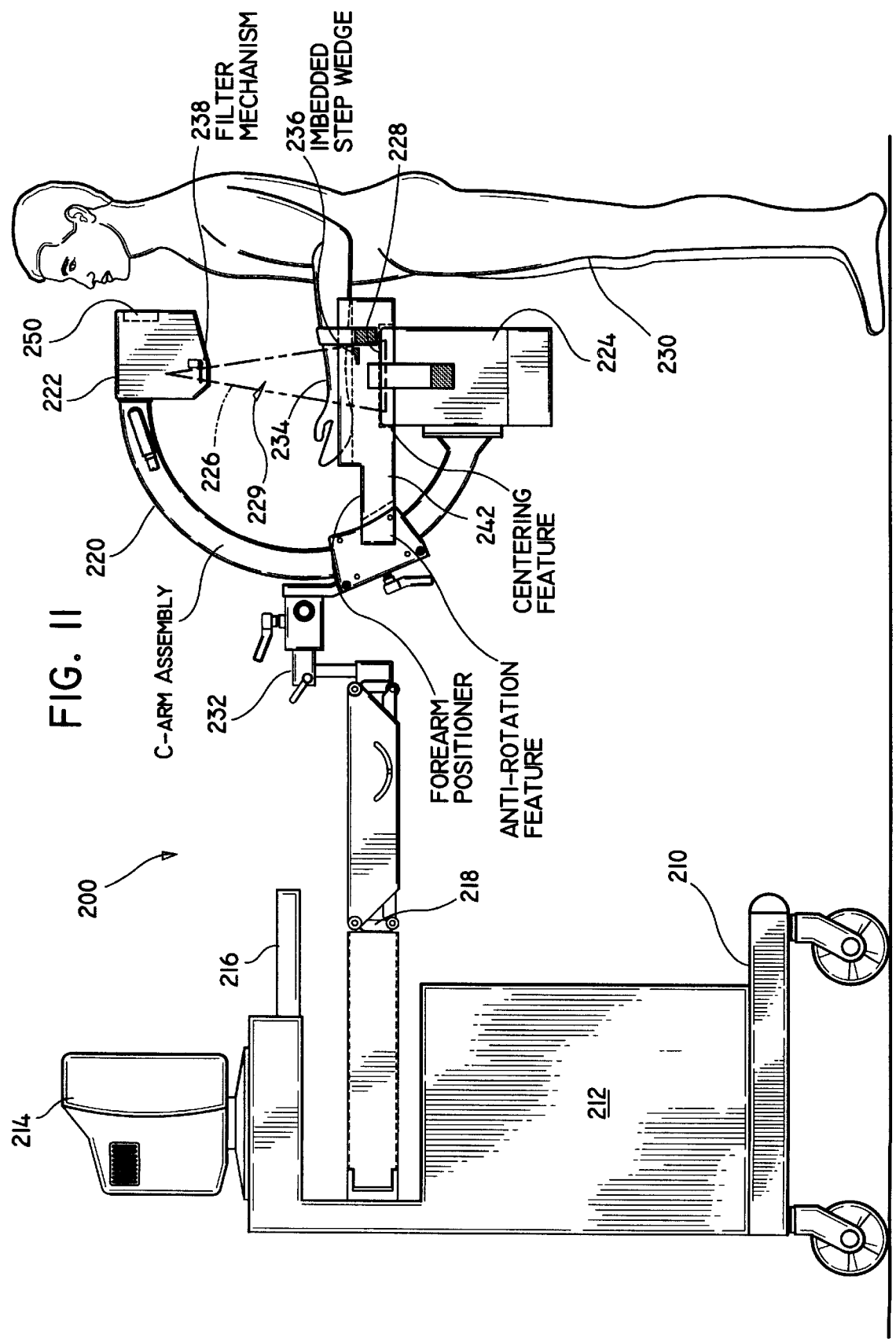

MINIATURE C-ARM APPARATUS WITH DUAL VIDEO DISPLAY MONITOR AND SINGLE DRIVER INTERFACE THEREFOR

CROSS REFERENCE TO RELATED APPLICATIONS

This application claims the priority benefit, under 35 U.S.C. §119(e)(1), of applicants' copending United States provisional applications Ser. No. 60/104,810, filed Oct. 19, 1998, and Ser. No. 60/109,968, filed Nov. 25, 1998, both of which are incorporated herein in their entirety by this reference.

BACKGROUND OF THE INVENTION

This invention relates to mobile x-ray fluoroscopic imaging systems with miniature C-arm apparatus, and more particularly to miniature C-arm apparatus having a dual video display monitor including two displays (e.g., two SVGA multiscan CRTs) mounted in a single rotating enclosure, which provides certain functions of the imaging system. Further, the invention in an important aspect is directed to mobile x-ray fluoroscopic imaging systems with miniature C-arm apparatus having a dual video display monitor using a single driver interface for 100% synchronous operation of both displays.

As used herein, the noun "display" (or "video display") means the face of a cathode ray tube (CRT). A monitor having two displays is sometimes referred to herein as a dual video display monitor.

In present-day medical practice, x-ray fluoroscopic imaging systems provide images of bone and tissue that are similar to conventional film x-ray shadowgrams but are produced by conversion of an incident x-ray pattern to a "live" enhanced (intensified) optical image that can be displayed on a video monitor directly, i.e., essentially contemporaneously with the irradiation of the patient's body or body portion being imaged. The term "fluoroscopic imaging" is used herein to designate such provision of directly video-displayed x-ray images. An imaging device, including an image intensifier, suitable for use in such a system is described in U.S. Pat. No. 4,142,101, which is incorporated herein in its entirety by this reference.

In some x-ray fluoroscopic imaging systems, the entire system is carried on an easily movable cart and an x-ray source and detector are mounted on a rotatable mini C-arm dimensioned for examining smaller body parts such as the extremities (wrists, ankles, etc.) of a human patient.

One illustrative example of a commercially available mini C-arm x-ray fluoroscopic imaging system is that sold under the trade name "FluoroScan III" by FluoroScan Imaging Systems, Inc., of Northbrook, Illinois. Further examples of mini C-arm x-ray fluoroscopic imaging systems are described in U.S. Pat. No. 5,627,873 and in copending U.S. patent application Serial No. 09/199,952 (filed Nov. 24, 1998 and assigned to the same assignee as the present application), both of which are incorporated herein in their entirety by this reference.

Mini C-arm x-ray fluoroscopic imaging systems are also being used to measure bone mineral density (BMD) of bones in, for example, the forearm or wrist, or in the ankle or heel (calcaneal region) of a human patient. An example of such an x-ray fluoroscopic imaging system is described in allowed copending U.S. patent application Ser. No. 08/794,615 (filed Feb. 3, 1997 and assigned to Hologic, Inc., the parent company of the assignee of the present application), which is incorporated herein in its entirety by this reference.

Generally, such mini C-arm x-ray fluoroscopic imaging systems and x-ray bone densitometry systems are economical in space, conveniently movable (as within a hospital, clinic or physician's office) to a desired temporary location of use, and offer superior safety (owing to low levels of electric current utilization and reduced exposure of personnel to scatter radiation) as well as ease of positioning the x-ray source and detector relative to a patient's extremity for imaging. The various functions and operations of the system are conventionally controlled by buttons or switches on a control panel that is positionally associated with the cart.

X-ray fluoroscopic imaging systems of the type with which the present invention is concerned typically include a processing system, such as a computer, and peripheral devices enclosed within a portable cabinet and a C-arm apparatus that is mounted to the cabinet. The processing system controls the operation of the various components of the imaging system, provides a camera or image processing to transform in real time image data received from an image receptor for display, printing or storage, and communicates with peripheral devices. The computer may also be configured to communicate with a local area network to transfer, for example, image data to locations remote from the sterile environment. An example of a suitable processing system is a personal computer running the Windows 95®, DOS, UNIX, MacOS or other operating systems. Examples of peripheral devices include display monitors, image (or video) printers and image storage devices (or recorders).

The C-arm apparatus includes a C-arm assembly, a support arm assembly and an articulated arm assembly. The C-arm assembly includes a C-arm having a track for guiding rotational movement of the C-arm, an x-ray source assembly including an x-ray source and an x-ray detector assembly including an image receptor and camera. The x-ray source and detector assemblies are located at opposing ends of the C-arm so that the x-ray source and image receptor face each other and x-rays emitted by the x-ray source impinge on the image receptor.

The support arm assembly engages the C-arm track so that the C-arm is movable relative to the support arm, and the articulated arm assembly is provided to facilitate movement of, including change in the angular orientation of, the source and detector assemblies relative to a patient's body portion being imaged.

The articulated arm assembly includes at least one movable arm wherein a first end portion of the arm is connected to the support arm assembly and a second end portion of the arm is connected to a mobile base or portable cabinet. Preferably, the first end portion is so connected to the support arm assembly that the support arm assembly can be rotated relative to the movable arm.

During surgical procedures a sterile field is created around a patient to ensure that foreign substances or organisms do not infect the patient. Any instruments or persons within this field have to be sterile or covered by a sterile draping material. The sterile field is generally defined by the American College of Surgeons and published by the Association of Operating Room Nurses (AORN). Generally, the sterile field is defined as the area occupied by the sterile draping material on any operating room table, including the patient table and instrument tables. To permit sterile personnel to position the x-ray fluoroscopic imaging system C-arm assembly in the sterile field a clear surgical drape covers the C-arm assembly.

In the x-ray fluoroscopic imaging system described in U.S. provisional patent application Ser. No. 60/078,491

(filed Mar. 18, 1998), and in U.S. patent application Ser. No. 09/270,373 (filed Mar. 16, 1999), the entire disclosures of which are both incorporated herein by this reference, to permit surgeons to activate certain functions of the x-ray fluoroscopic imaging system within this sterile field, either the x-ray source assembly or the x-ray detector assembly, which are used within the sterile field, includes a control panel that provides a physician with easy access to pre-defined imaging control functions associated with the x-ray fluoroscopic imaging system within the sterile field. By locating the control panel on the ends of the C-arm, a surgeon can activate the functions without placing a hand or arm in the path of the x-ray beam. Preferably, the control panel includes an array of membrane switches, wherein each switch in the array is provided to activate a function performed by the x-ray fluoroscopic imaging system. Examples of functions controlled by the control panel switches include: x-ray source activation; image printing; image noise suppression; camera rotation; and x-ray source voltage/current control.

The x-ray fluoroscopic imaging system may also include a foot control panel which is similar to the above-described control panel but permits foot activation of predefined functions of the x-ray fluoroscopic imaging system including but not limited to x-ray activation, image printing and image storing.

Typically or preferably, present-day miniature C-arm x-ray fluoroscopic imaging systems have dual video display monitors.

SUMMARY OF THE INVENTION

The present invention, in a first aspect, broadly contemplates the provision of an x-ray fluoroscopic imaging system comprising a portable cabinet; a support arm assembly; a video monitor comprising two video displays; an articulated arm assembly having at least one movable arm and connecting the support arm assembly to the cabinet; and a C-arm assembly having a C-arm carried by the support arm assembly, an x-ray source assembly including an x-ray source and an x-ray detector assembly including an image receptor located at opposing locations on the C-arm such that the x-ray source and image receptor face each other so that x-rays emitted by the x-ray source impinge on the image receptor; wherein the improvement comprises a single rotatable enclosure mounting the two video displays to display images required by the fluoroscopic imaging system. Preferably, the rotatable enclosure provides rotation of about 40°.

In a further aspect, the invention embraces the provision of an x-ray fluoroscopic imaging system comprising a portable cabinet; a support arm assembly; a video monitor comprising two video displays; an articulated arm assembly having at least one movable arm and connecting the support arm assembly to the cabinet; and a C-arm assembly having a C-arm carried by the support arm assembly, an x-ray source assembly including an x-ray source and an x-ray detector assembly including an image receptor located at opposing locations on the C-arm such that the x-ray source and image receptor face each other so that x-rays emitted by the x-ray source impinge on the image receptor; wherein the improvement comprises a single driver interface for the two video displays for 100% synchronous operation of both video displays to display images required by the fluoroscopic imaging system.

In the single driver interface of the system of the invention, the circuitry resides on two PCBs. Advantageously or preferably, the displays are dual SVGA multiscan CRTS. Further in accordance with the invention, in preferred embodiments thereof, the two displays may have individual yokes, video processor PCBs, and power supplies. Also, the monitor may comprise two displays with IR sensor window for IR control.

Further features and advantages of the invention will be apparent from the detailed description hereinbelow set forth, together with the accompanying drawings.

BRIEF DESCRIPTION OF THE DRAWINGS

FIGS. 5A, 5B and 5C are views respectively in side elevation, front elevation and plan of the apparatus of FIG. 1;

FIG. 11 is a simplified and partly schematic side elevational view of a mini C-arm x-ray fluoroscopic imaging system arranged for use to measure forearm BMD of a human patient, in which an embodiment of the present invention may be incorporated.

DETAILED DESCRIPTION

Figure 1:
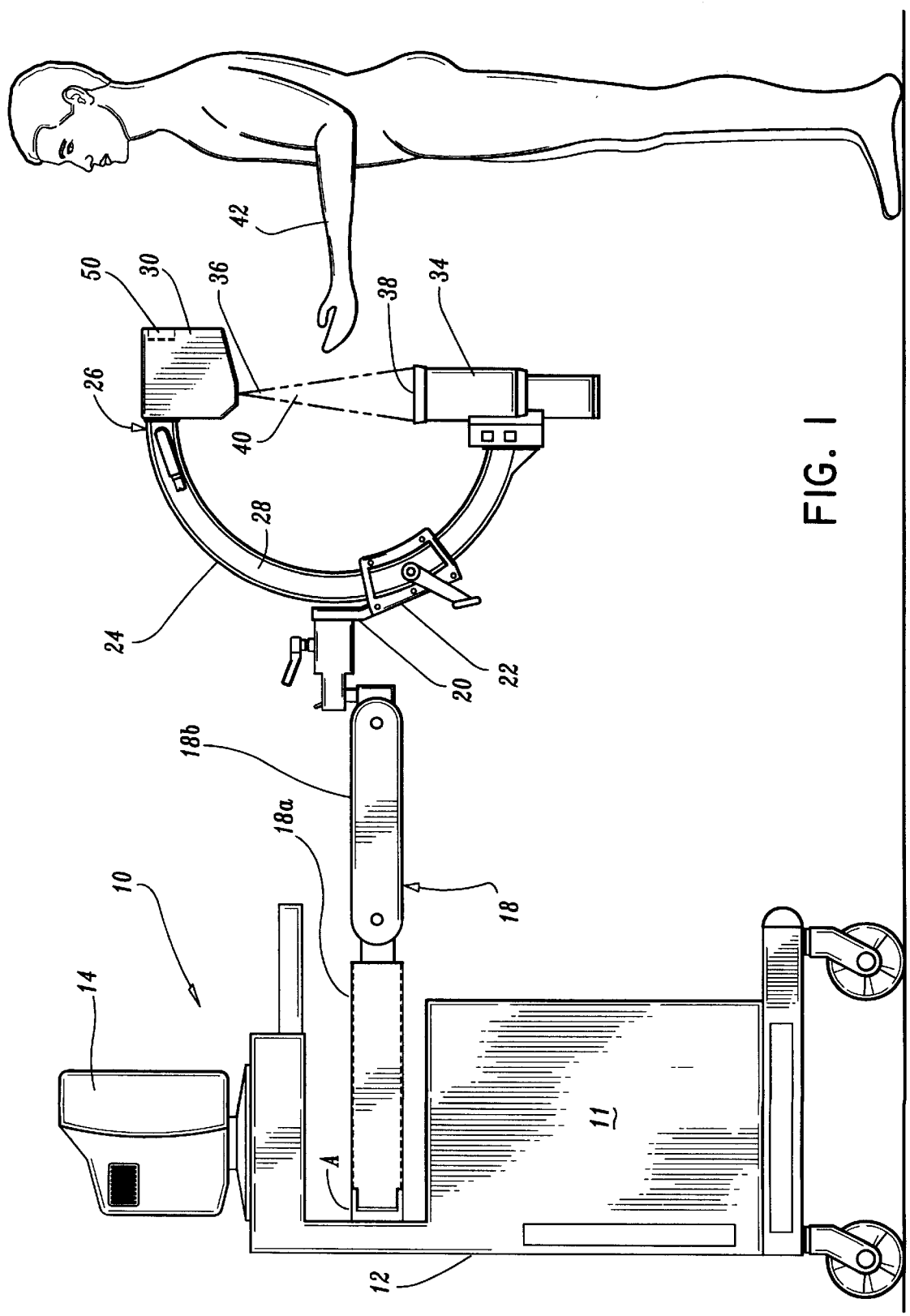
FIG. 1 is a simplified and partly schematic side elevational view of mini C-arm x-ray fluoroscopic imaging apparatus, including a monitor having two video (CRT) displays, and incorporating an illustrative embodiment of the present invention.
Figure 2:
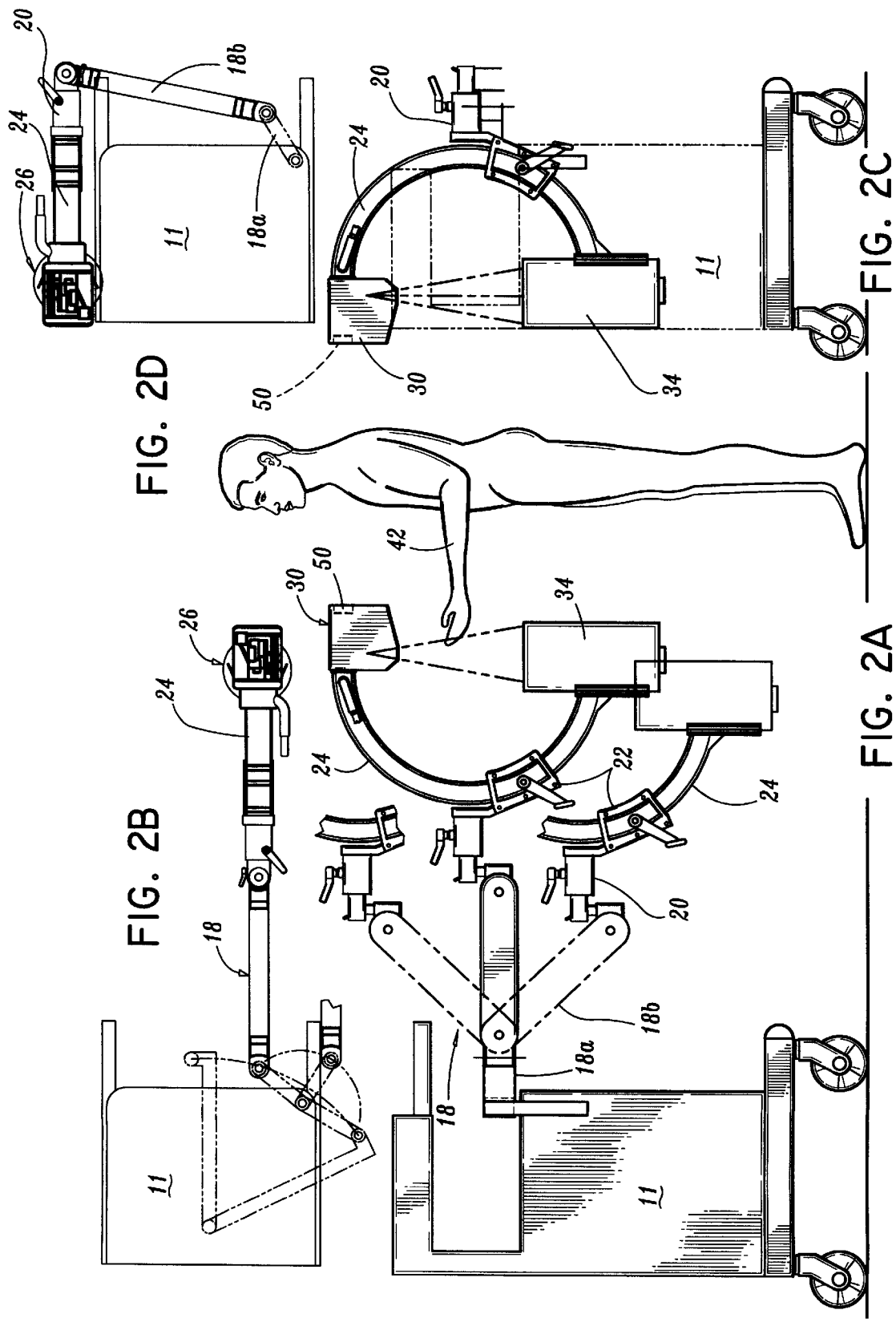
FIGS. 2A, 2B, 2C and 2D are reduced-scale views of the apparatus of FIG. 1, respectively in side elevation with the arm assembly extended (showing different positions thereof), in plan with the arm assembly extended, in side elevation with the arm assembly folded, and in plan with the arm assembly folded.
Figure 3:
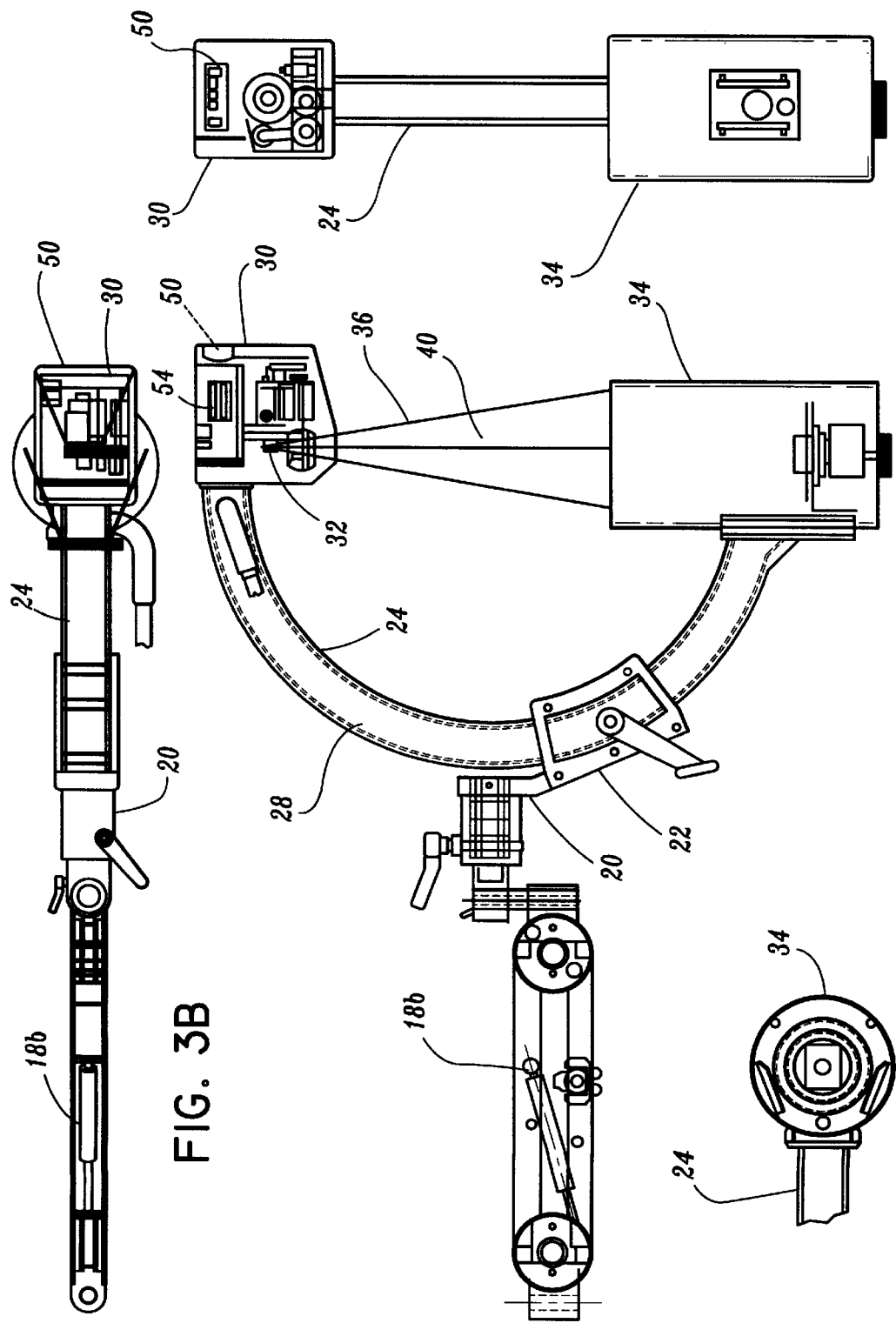
FIGS. 3A, 3B, 3C and 3D are enlarged views of a portion of FIG. 1, respectively in side elevation, top plan, fragmentary bottom plan, and front elevation.
Figure 4:
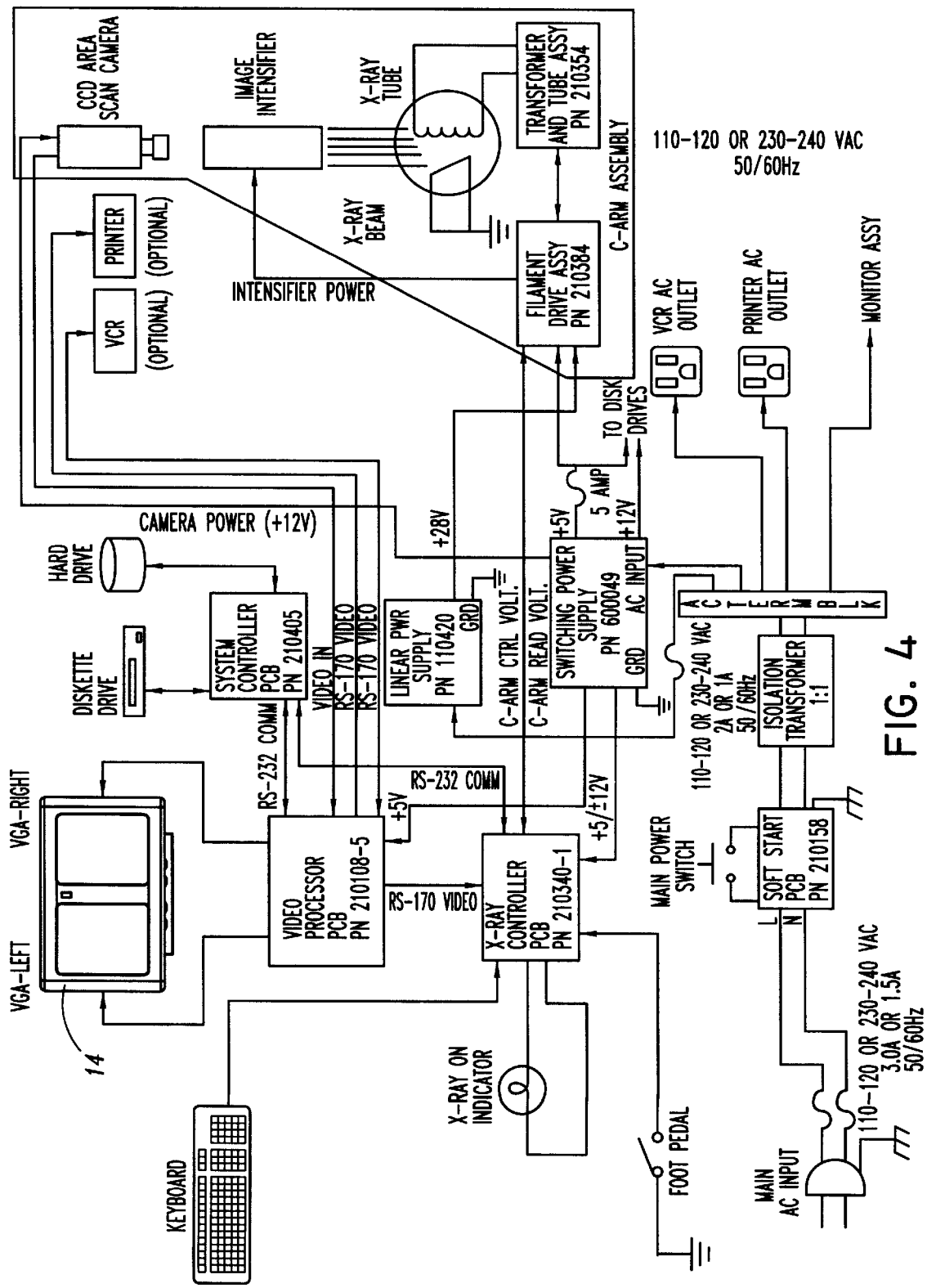
FIG. 4 is a system block diagram of the apparatus of FIG. 1.

An exemplary x-ray fluoroscopic imaging system incorporating one embodiment of the present application is shown in FIGS. 1–5. In this embodiment, the imaging system 10 is entirely contained in a wheeled cart or portable cabinet 11 that can easily be rolled from place to place. The cabinet includes a generally rectangular, upright body 12 that supports a monitor 14 constituted of two video displays 14a and 14b on its top surface and an articulated arm assembly 18 secured thereto. The cabinet also contains a computer for processing data. It will be understood that images taken by the imaging system can be shown on only a single display, or printed on a printer which is preferably enclosed within the cabinet.

In this embodiment, the articulating arm assembly 18 includes two arms 18a and 18b. The distal end of arm 18b is connected to a support arm assembly 20 that has a C-arm locking mechanism 22. A C-arm 24 of mini C-arm assembly 26 is carried by the support arm assembly 20 such that a track 28 of the C-arm is slidable within the C-arm locking mechanism 22. The mini C-arm assembly 26 also includes an x-ray source assembly 30 and an x-ray detector assembly 34 respectively mounted at opposite extremities of the C-arm in facing relation to each other so that an x-ray beam 36 from an x-ray source 32 within the source assembly impinges on the input end 38 of the detector assembly 34. The x-ray source 32 and detector end 38 are spaced apart by the C-arm sufficiently to define a gap 40 between them, in which the limb or extremity of a human patient 42 can be inserted in the path of the x-ray beam 36.

The support arm assembly 20 connected to the end of arm 18b provides 3-way pivotal mounting that enables the C-arm 24 to be swivelled or rotated through 360° in each of three mutually perpendicular (x, y, z) planes and to be held stably at any desired position, while the arm 18a of the articulating arm assembly 18 is mounted to the portable cabinet 11 at point "A" and jointed to enable its distal end and the C-arm to be angularly displaced both horizontally and vertically. The multidirectional angular movability of the C-arm assembly facilitates the positioning of the x-ray source and detector assemblies in relation to a patient body portion to be irradiated.

A suitable power supply (not shown) for the x-ray source, and instrumentalities (also not shown) for controlling or varying current (mA) and voltage (kV), are incorporated in the system as well.

As noted, the C-arm 24 is movable within the C-arm locking mechanism 22. To fix the position of the C-arm relative to the support arm assembly 20, the C-arm locking mechanism is used. The C-arm locking mechanism may be a clamp assembly (not shown) which is compressed against the C-arm when tightened, but preferably the C-arm locking mechanism is of the type described in pending U.S. Provisional Patent Application No. 60/066,966 filed on Nov. 28, 1997, which is incorporated herein in its entirety by this reference.

Preferably, either the x-ray source assembly or the x-ray detector assembly includes a control panel 50 that is mounted thereon (i.e. at one or the other of the opposed extremities of the C-arm) and is coupled to the imaging system computer to provide a physician with easy access within the sterile field to predefined imaging control functions associated with the x-ray fluoroscopic imaging system. With the control panel 50 included in either the source or detector assembly, a physician can activate certain (or all) functions of the x-ray fluoroscopic imaging system from within the sterile field and without placing a hand or arm within the path of the x-ray beam. One result of this configuration is that it gives a physician immediate control of the operating characteristics of the fluoroscope in the event that a regular operator is unavailable or unable to operate controls located outside of the sterile field.

In the exemplary system illustrated in the drawings, the control panel has an array of switches, one of which controls the x-ray source to generate a single image or for continuous imaging. For example, to generate a single image, a physician may depress the x-ray control switch twice in rapid succession and then release the switch so that the x-ray source (or tube) is activated for a single image or strobe shot. For continuous imaging, a physician depresses the x-ray control switch twice in rapid succession and then continues to depress (or hold down) the switch so that the x-ray source is activated and continues to produce x-rays for as long as the switch is depressed to create a real time continuous or cinematic fluoroscopic picture.

As thus far described, the system 10 is essentially identical to currently available mini C-arm x-ray fluoroscopic imaging systems. Thus, the system 10 may be a "FluoroScan IV" system, produced by FluoroScan Imaging Systems, Inc., having the following specifications:

OUTPUT FORMAT:
  Standard 2,200 Image Storage;
  Optional 4,000 Image Storage; Digital Video Output;
  Composite Video Output Video Standard NTSC/VHS
VIDEO PROCESSING:
  Last Image Hold for 4 Images;
  Real Time Edge Enhancement;
  User Selectable Real Time Recursive Averaging;
  Noise Suppression; Automatic Contrast Enhancement;
  Automatic Brightness Control
INPUT POWER:
  110V~60 Hz Nominal; 90V~ to 132V~ Actual; 47 Hz to 63 Hz Actual; Non Dedicated, Grounded
WARM UP: 3 Seconds
X-RAY POWER SUPPLY:
  Continuous Duty kV–40 kV to 75 kV in 2.15 kV Increments
ANODE CURRENT:
  20 $\mu$A (0.020 mA) to 100 $\mu$A (0.1 mA) in 3.6 $\mu$A Increments
FOCAL SPOT: 85 Micron (0.085 mm)
TUBE TYPE: Custom Designed Cold Anode
TUBE COOLING:
  Maximum Tube Temperature is 50° C. at Maximum Power
  After 4 Hours of Continuous Duty
TARGET: Tungsten
COLLIMATION: Fixed to Field of View Size
FIELDS OF VIEW: 150 mm (6" Nominal)
IMAGE INTENSIFIER:
  High Gain Micro Channel Plate with Minimum of 40,000 Gain
PIXEL ARRAY: 768 pixels by 600 lines
MONITOR:
  15" (39 cm) SVGA High Resolution Video Displays (two)
OVERALL HEIGHT: 60 inches
OVERALL FLOOR SPACE: 8.0 ft$^2$ (36" wide by 32" deep)

Figure 6A:
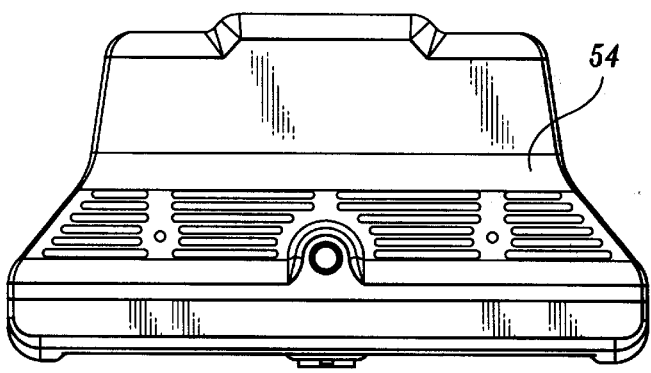
FIGS. 6A, 6B, 6C and 6D are, respectively, top plan, side elevational, front elevational and bottom plan views of the monitor including the two displays mounted on the cabinet of the imaging system of FIGS. 1–3.
Figure 6B:
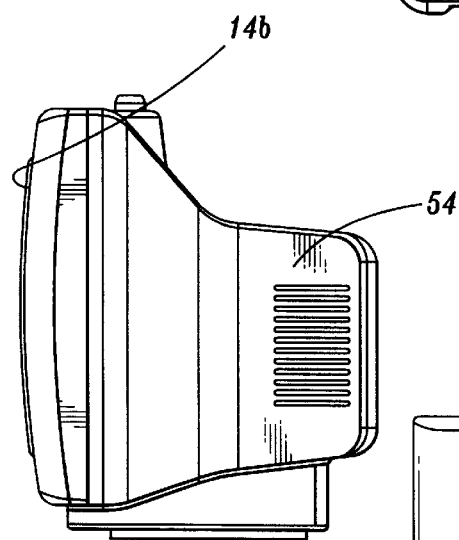
Figure 6C:
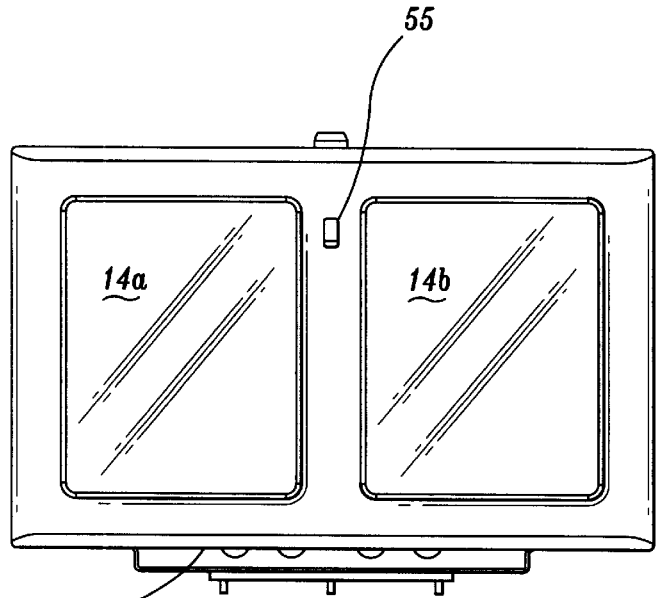
Figure 6D:
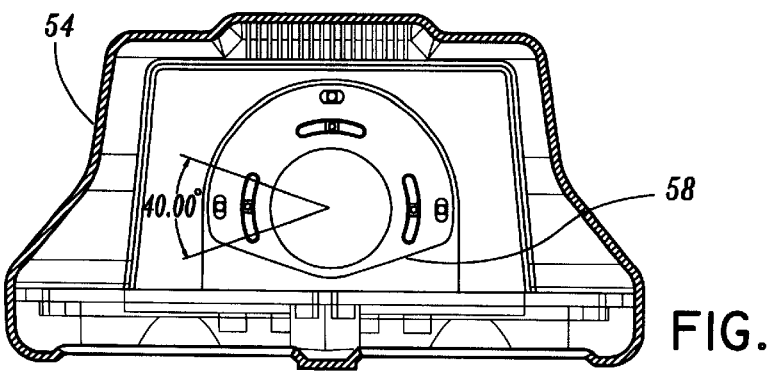

More particularly, the two video displays 14a and 14b are SVGA multiscan CRTs. As shown in FIGS. 6A, 6B, 6C and 6D, in accordance with the present invention, in its illustrated embodiment, these two displays are mounted vertically together in a single rotatable enclosure 54 (a rigid molded plastic structure with a rotatable mounting) to display the images required by the fluoroscopic imaging system. That is to say, the enclosure 54 encases two high-resolution monochrome displays, monitor controls 57 being located as indicated in FIG. 6C. These are two 15-inch displays with individual yokes, video processor PCBs, and common driver board and low voltage power supplies. They can be displays with IR sensor window 55 for IR sensor control. Each of the two displays in FIG. 6 has the following pertinent specifications:

DISPLAY SIZES
- 15 inches
- Portrait orientation
- 13.3 inches diagonal
- 8.5 inches horizontal
- 11.0 inches vertical DISPLAY CHARACTERISTICS
- P4 phosphor
- 554 pixels×416 line resolution
- 120 fL brightness
- 5% linearity
- 3% raster regulation RELIABILITY
- 25,000 hour minimum MECHANICAL
- 25 pounds weight ENVIRONMENTAL
- +5° C. to +40° C. (operating)
- 20% to 80% humidity
- 0 to 10,000 feet altitude (operating)

Figure 6E:
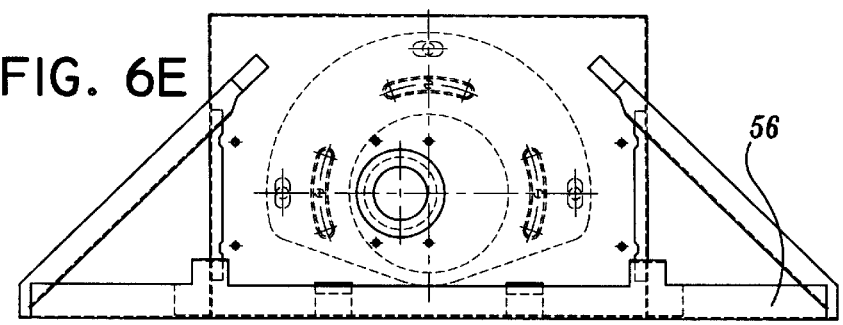
FIGS. 6E, 6F and 6G are, respectively, plan, side elevational and front elevational views of the monitor frame assembly of an exemplary embodiment of the invention, showing the mounting details.
Figure 6I:
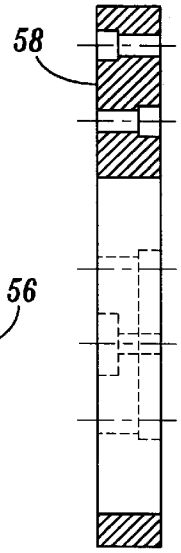
FIGS. 6H and 6I are, respectively, a plan view of the swivel bearing pad that provides angular rotation capability of 40° in the described embodiment, and a sectional view taken along the line 6I—6I of FIG. 6H.
Figure 6G:
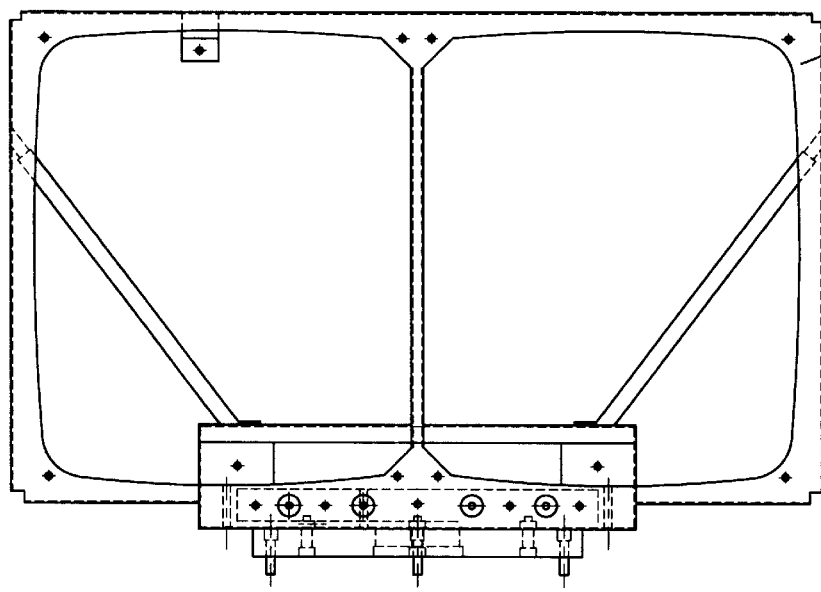
Figure 6F:
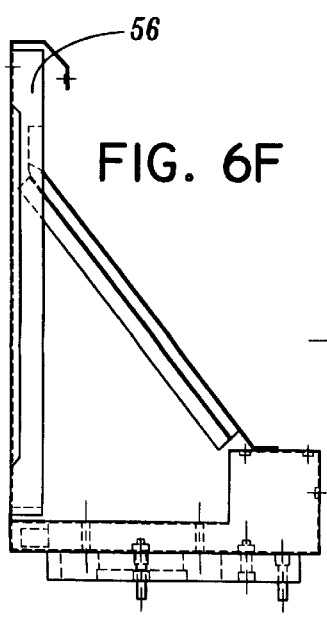
Figure 6H:
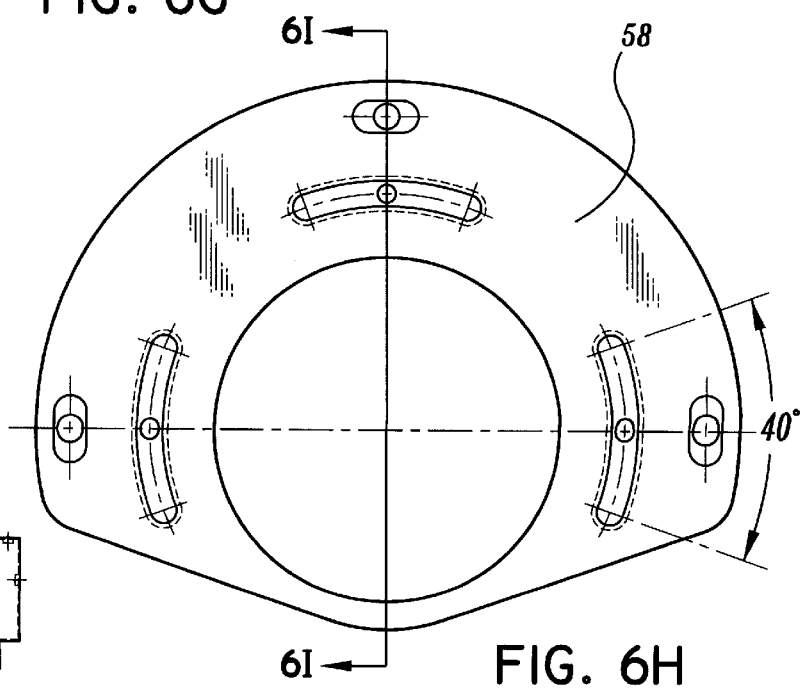

FIGS. 6E, 6F and 6G illustrate the monitor frame assembly 56 showing the mounting details. The frame is spot welded or arc welded as required to produce a rigid assembly of dual displays. Each display is mounted in the vertical position, as opposed to the horizontal position of a display. This provides the surgeon with the best display possible from all angles. FIGS. 6H and 6I illustrates the swivel bearing pad 58 that provides 40° adjustability (rotatability about a vertical axis) of the system for ease of viewing.

The described embodiment of the invention provides a monitor assembly that is modular, has high resolution 15-inch twin displays, and is easily adjustable for the surgeon's viewing of the x-ray output.

Figure 7:
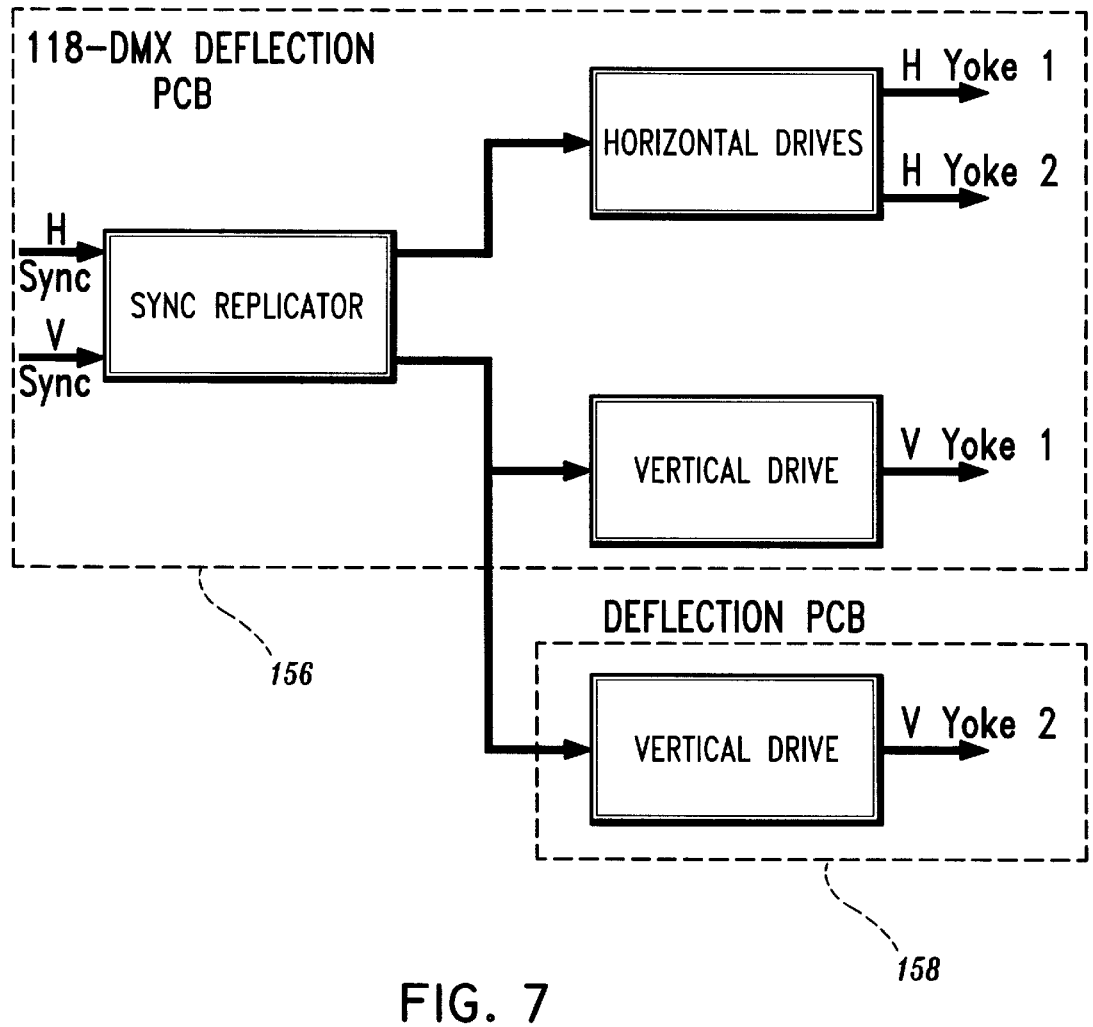
FIG. 7 is a block diagram of an example of the deflection PCBs and their interaction with the C-arm system electronics, illustrating an exemplary embodiment of the invention.

Further in accordance with the invention, in its illustrated embodiment, the monitor uses a single driver interface (FIG. 7) for 100% synchronous operation of both displays to display the images required by the fluoroscopic imaging system. The actual circuitry resides on two PCBs. FIG. 7 is a block diagram of an illustrative example of the two single driver interface PCBs (deflection PCBs) respectively designated 156 and 158 and their interaction with the C-arm system electronics. The monitor system incorporates a single power interface, dual SVGA display video interfaces, IR remote interface and x-ray on indicator interface, and, as a particular feature of the present invention, a single driver interface. This driver interface ensures 100% synchronous operation of both displays.

One illustrative but non-limiting example of the two deflection PCBs will now be specifically described.

118 DMX Deflection Board

Figure 8:
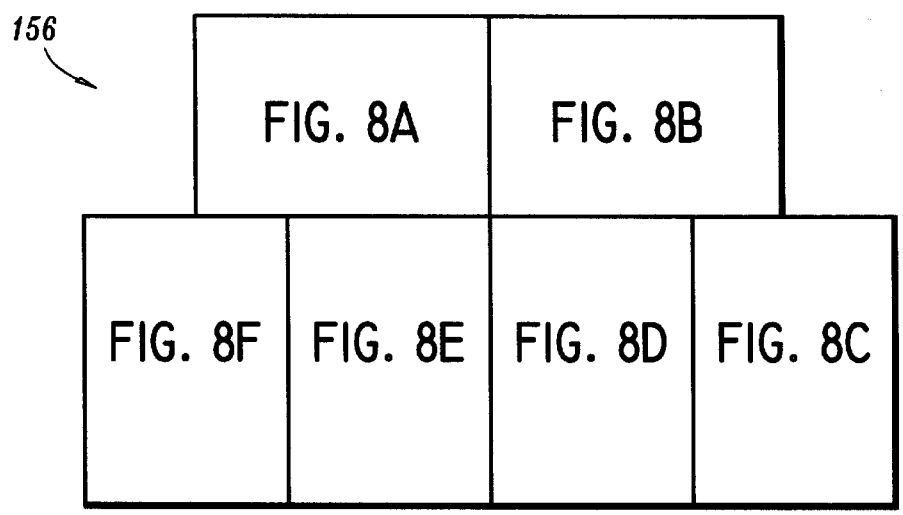
FIG. 8 is a block diagram showing the arrangement of views of FIGS. 8A–8F.

FIG. 8, in its various parts, is a schematic of the 118 DMX Deflection Board 156. This board utilizes a single horizontal sync input and generates horizontal drives for both horizontal deflection yokes. It provides power for the picture tube filaments and creates a dynamic focus for both tubes. This board also provides the vertical deflection for one of the picture tubes and sync for the other picture tube. The vertical drive portion of this board's circuitry is replicated on the other deflection board.

The bill of materials for this board is as follows:

118 DMX DEFLECTION BOARD BILL OF MATERIAL

| ITEM NUMBER | DESCRIPTION |
| --- | --- |
| R100 | 1K, 1W |
| R200 | 1K |
| R201 | 1K |
| R202 | 1K |
| R203 | 270 |
| R204 | 100 |
| R207 | 1K |
| R208 | 470 |
| R209 | 4.7K |
| R210 | 4.7K |
| R300 | 1K, 1W |
| R301 | 10K |
| R302 | 27K |
| R304A | 100 |
| R304B | 0 |
| R305A | 150 OHM, 2W |
| R305B | 150 OHM, 2W |
| R306 | 220 |
| R307 | 1.2K |
| R308 | 100K |
| R309 | 47K |
| R310 | 680 |
| R311 | .47, 1W |
| R312 | 1K, 1W |
| R400 | 20, 5W |
| R401 | 10K |
| R402 | 15K |
| R403 | 4.7K |
| R406 | 47K |
| R408 | 1K |
| R409 | 47 |
| R410 | 2.2K |
| R411 | 220 |
| R412 | .82, 1W |
| R415 | 18 |
| R417 | 270, 1W |
| R418 | 150, 1W |
| R419 | 2.2K |
| R420 | 4.7K |
| R421 | 180K |
| R422 | 6.8K |
| VR300 | 500 |
| VR400 | 5K |
| VR401 | 250K |
| VR402 | 100K |
| VR403 | 20K |
| C100 | 100 UF, 50V |
| C200 | 10 UF |
| C201 | 10 UF |
| C202 | .1 UF |
| C203 | .1 UF |
| C300 | 47 UF, 16V |
| C301 | 5600 PF |
| C302 | 4.7 UF, 50V |
| C303 | .0047 UF |
| C304 | .01 UF, 250V |
| C305 | 330 UF, 35V |
| C306 | 100 PF |
| C307 | .0047 UF |
| C310 | 390 PF |
| C311 | 1 UF |
| C313 | 100 UF, 50V |
| C314 | 0.012 UF |
| C315 | 0.012 UF |
| C316 | 0.012 UF |

-continued

| 118 DMX DEFLFECTION BOARD BILL OF MATERIAL | |
|---|---|
| ITEM NUMBER | DESCRIPTION |
| C317 | 0.012 UF |
| C318 | 150 UF, 160V |
| C319 | 47 UF, 50V |
| C400 | 1000 UF, 35V |
| C401 | .1 UF |
| C402 | 330 UF, 35V |
| C403 | 0.0047 PF |
| C405 | .1 UF |
| C406 | .1 UF |
| C407 | .1 UF |
| C408 | .15 UF |
| C409 | 47 UF, 16V |
| C410 | 1000 UF, 35V |
| C411 | 0.01 UF |
| C502 | 100 UF, 50V |
| C601 | .68 UF, 200V |
| C602 | .01 UF, 1KV |
| C603 | .01 UF |
| D100 | 1N5231 |
| D300 | 86-107-14 |
| D301 | 1N4740 |
| D302 | MUR8100E |
| D400 | 1N4007 |
| D402 | 1N4148 |
| D403 | FR157 |
| D502 | FR157 |
| Q300 | 2N6715 |
| Q301B | MJ116206 |
| Q401 | 2N4402 |
| Q402 | 2N4401 |
| IC200A | 74LS86 |
| IC300 | AN5435 |
| IC400 | TDA1675A |
| T300 | DRIVE TRANSFORMER |
| T301 | HORIZONTAL DEFLECTION YOKE |
| T600 | FOCUS |

Vertical Deflection Board

Figure 9:
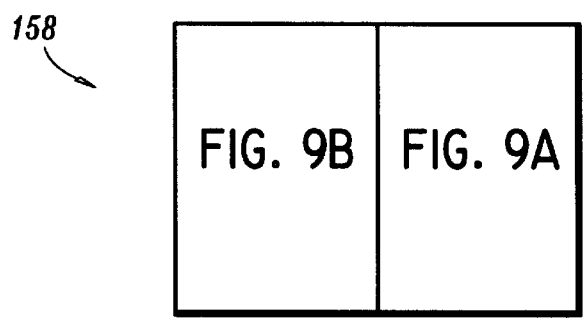
FIG. 9 is a block diagram showing the arrangement of views of FIGS. 9A–9B.

This board is used to provide the vertical drive for the second monitor. It is synced to the main deflector board through connector H401 receiving vertical sync as an input. The board provides controls for vertical hold, vertical linearity, and vertical centering for proper vertical adjustment. Its output is a vertical drive signal that has been processed through IC400 driving the yoke. The schematic for this board is shown in the various parts of FIG. 9. Its bill of materials is as follows:

| DEFLECTION BOARD BILL OF MATERIAL | |
|---|---|
| ITEM NUMBER | DESCRIPTION |
| R400 | 20 OHM, 5W |
| R401 | 10K |
| R402 | 15K |
| R403 | 4.7K |
| R405 | 560K |
| R406 | 47K |
| R407 | 2.2 |
| R408 | 1K |
| R409 | 47 |
| R410 | 2.2K |
| R411 | 220 |
| R412 | .82 OHM, 1W, METAL OXIDE |
| R415 | 18 |
| R417 | 270 |
| R418 | 150 |

-continued

| DEFLECTION BOARD BILL OF MATERIAL | |
|---|---|
| ITEM NUMBER | DESCRIPTION |
| R419 | 1K |
| R420 | 2.2K |
| R421 | 10K |
| R422 | 6.8K |
| R423 | 180K |
| VR400 | 5K |
| VR401 | 250K |
| VR402 | 100K |
| VR403 | 10K |
| C400 | 1000 UF, 35V |
| C401 | .1 UF |
| C402 | 220 UF, 35V |
| C404 | .33 UF, 35V |
| C405 | .1 UF |
| C406 | .1 UF |
| C407 | .1 UF |
| C408 | .15 UF |
| C409 | 47 UF, 16V |
| C410 | 1000 UF, 35V |
| C411 | 0.01 UF |
| C415 | 1000 UF, 35V |
| C416 | .1 UF |
| D400 | 1N4007 |
| D402 | 1N4148 |
| Q401 | 2N4402 |
| Q402 | 2N4402 |
| IC400 | TDA 1675 |

Figure 10:
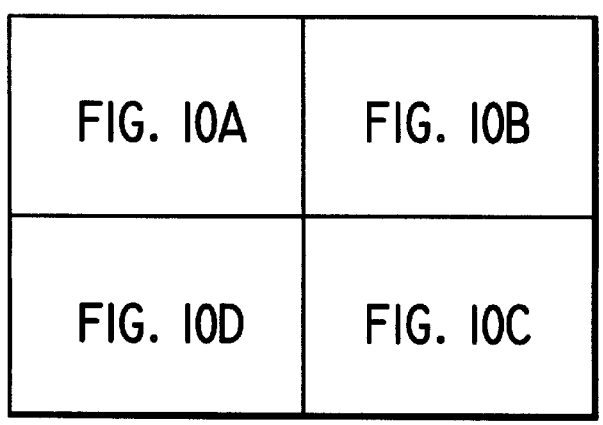
FIG. 10 is a block diagram showing the arrangement of views of FIGS. 10A–10D.
Figure 8A:
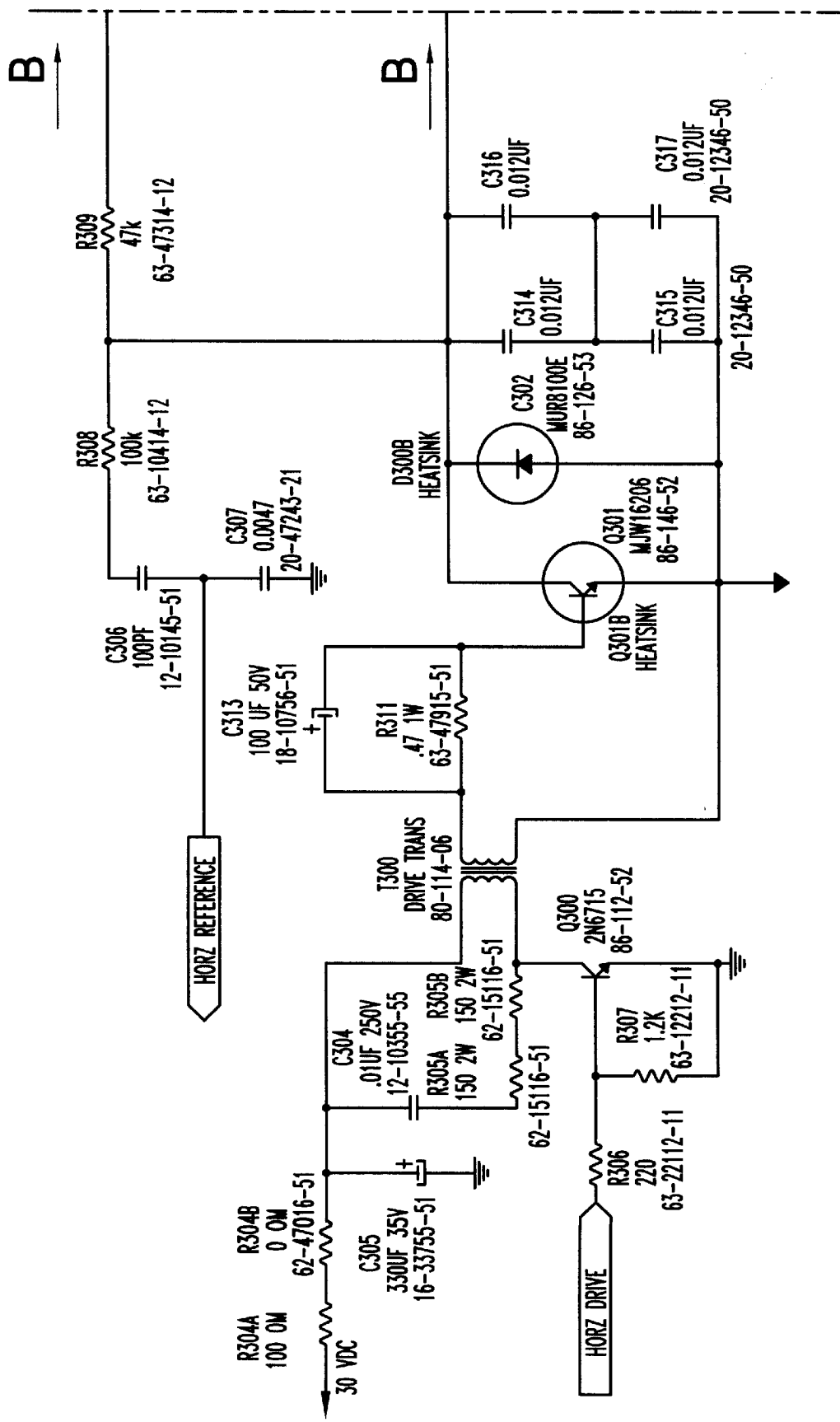
FIGS. 8A–8F, collectively, arranged as shown in FIG. 8, constitute a schematic of an example of the 118 DMX Deflection Board providing horizontal and vertical drivers.
Figure 8B:
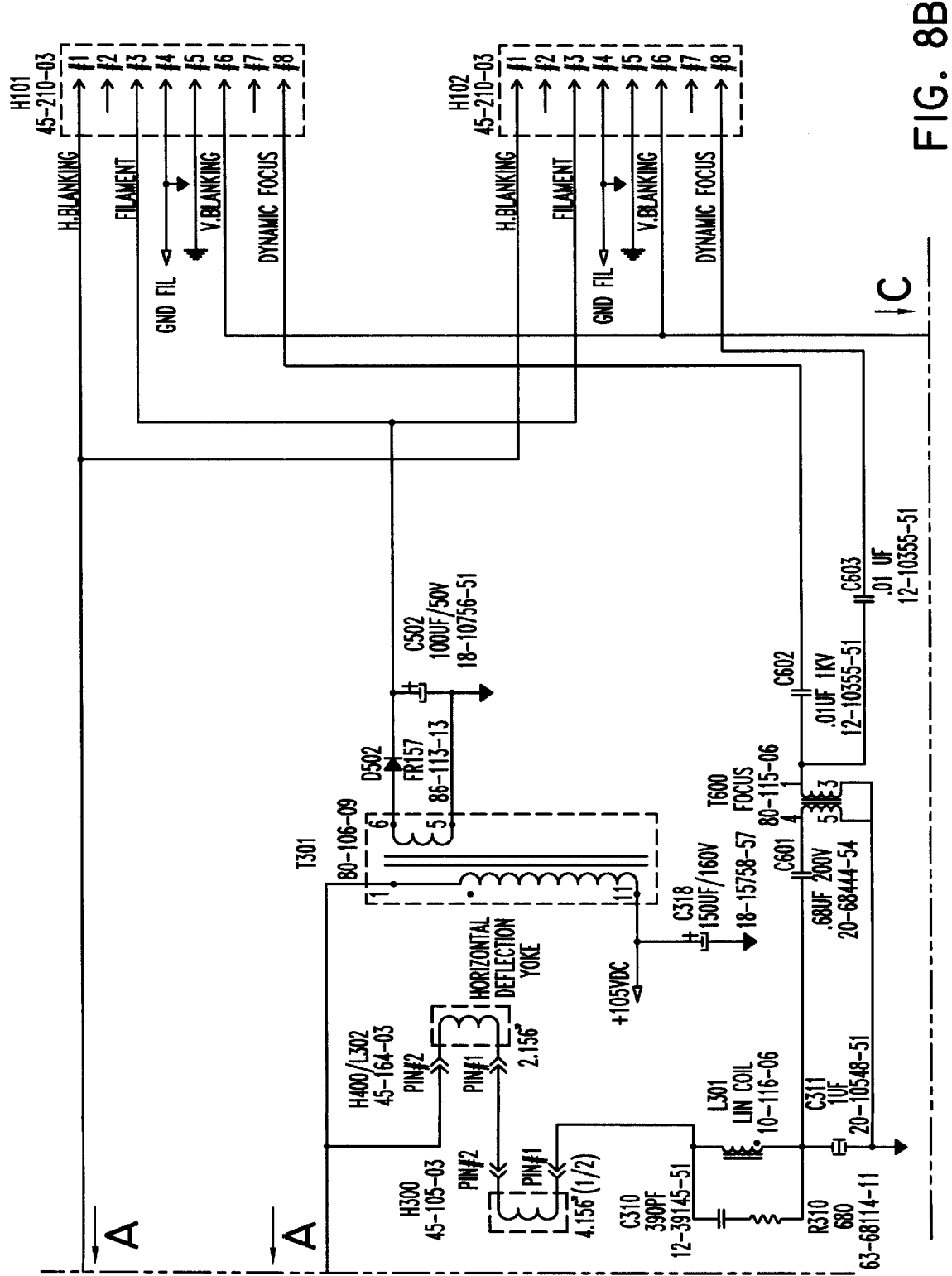
Figure 8C:
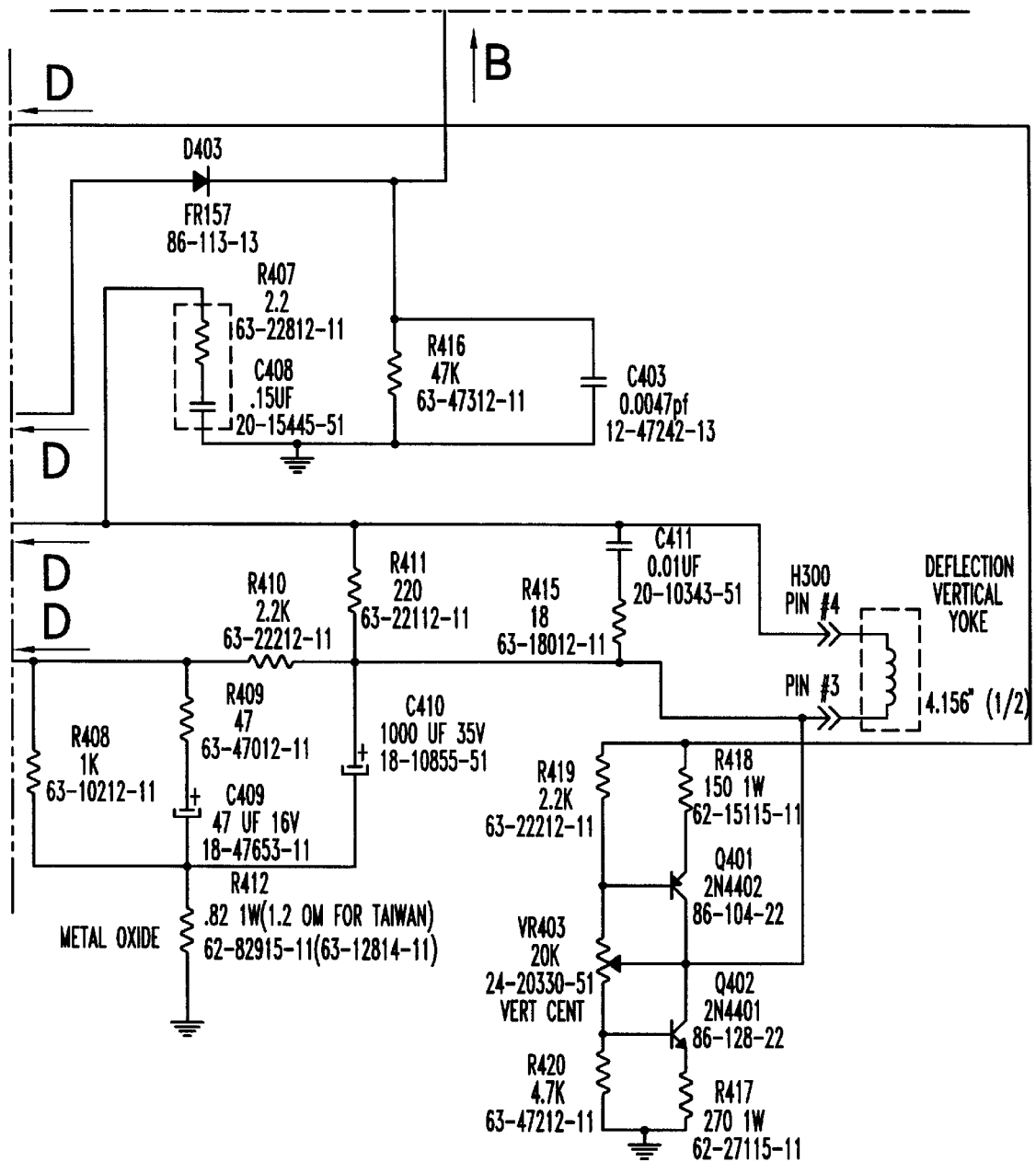
Figure 8D:
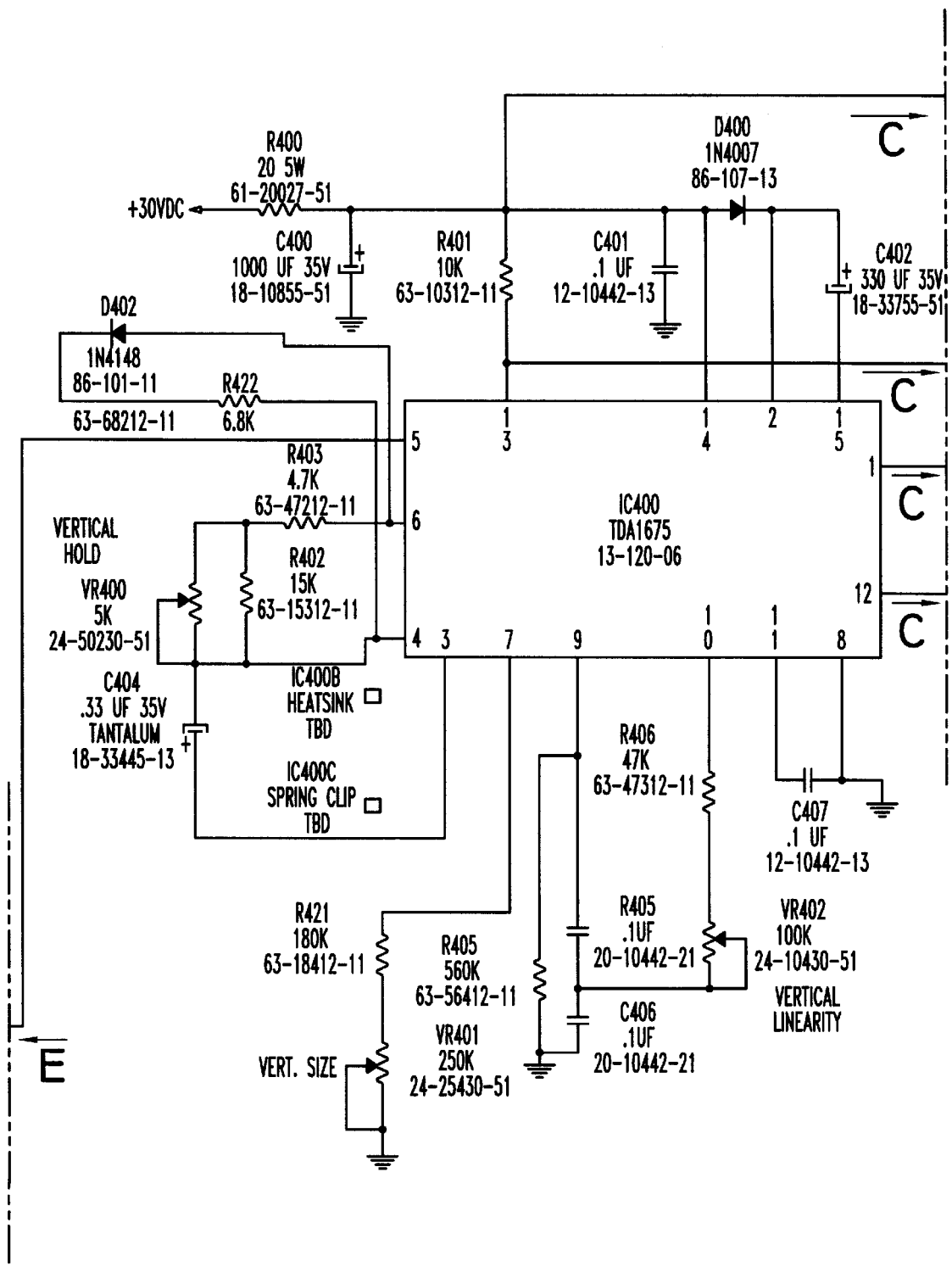
Figure 8E:
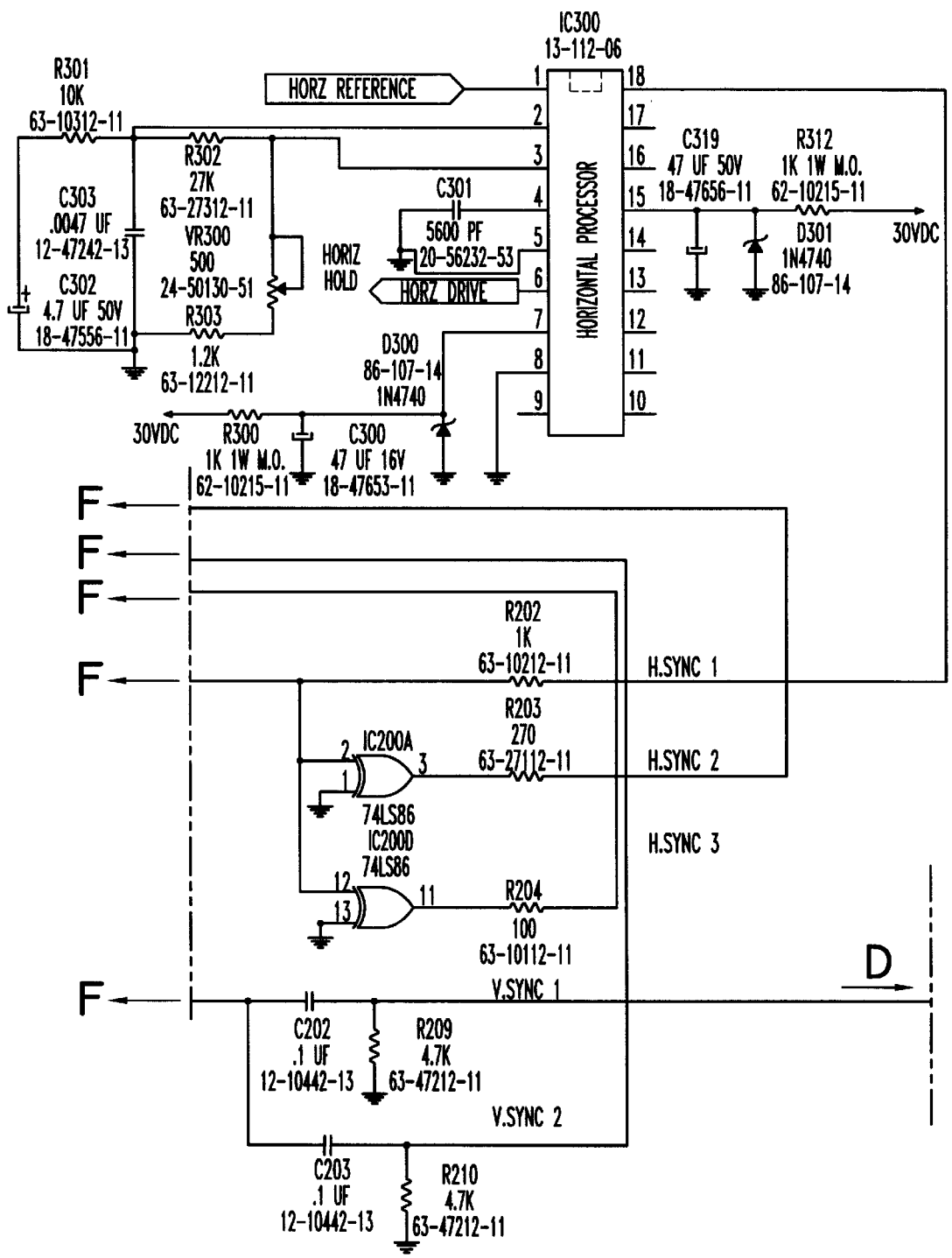
Figure 8F:
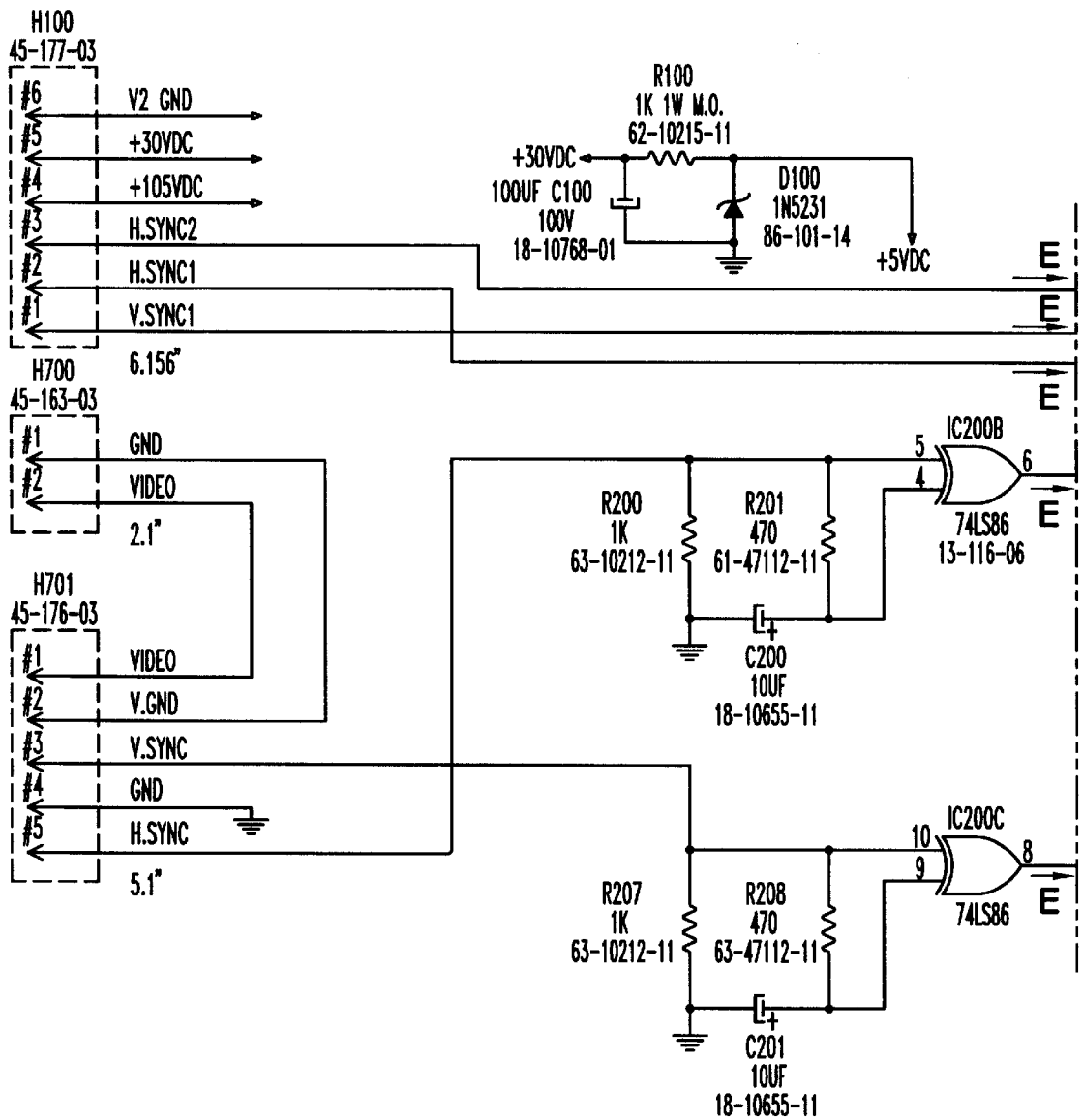
Figure 9A:
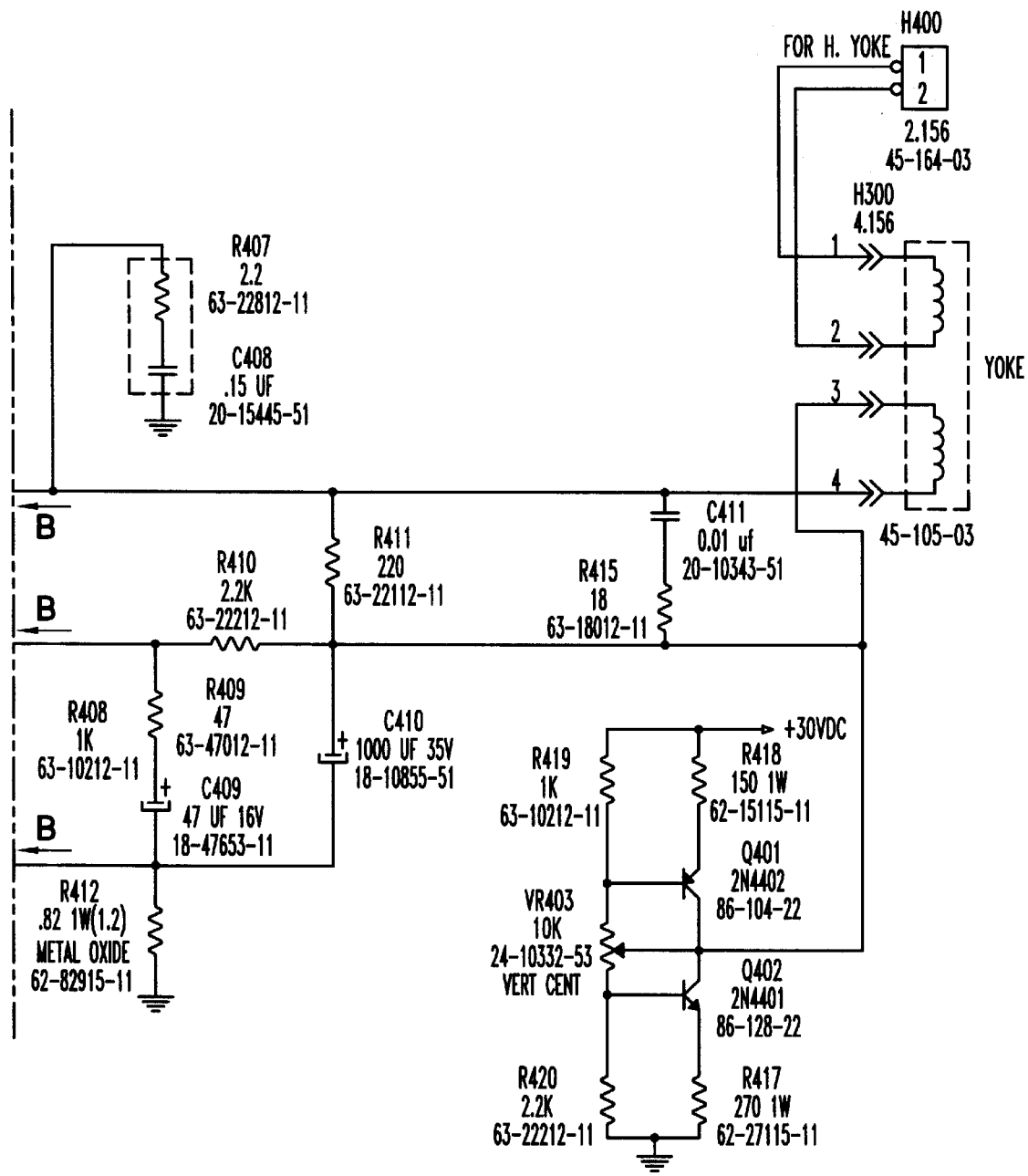
FIGS. 9A and 9B, collectively, arranged as shown in FIG. 9, constitute a schematic of an example of the Vertical Deflection Board.
Figure 9B:
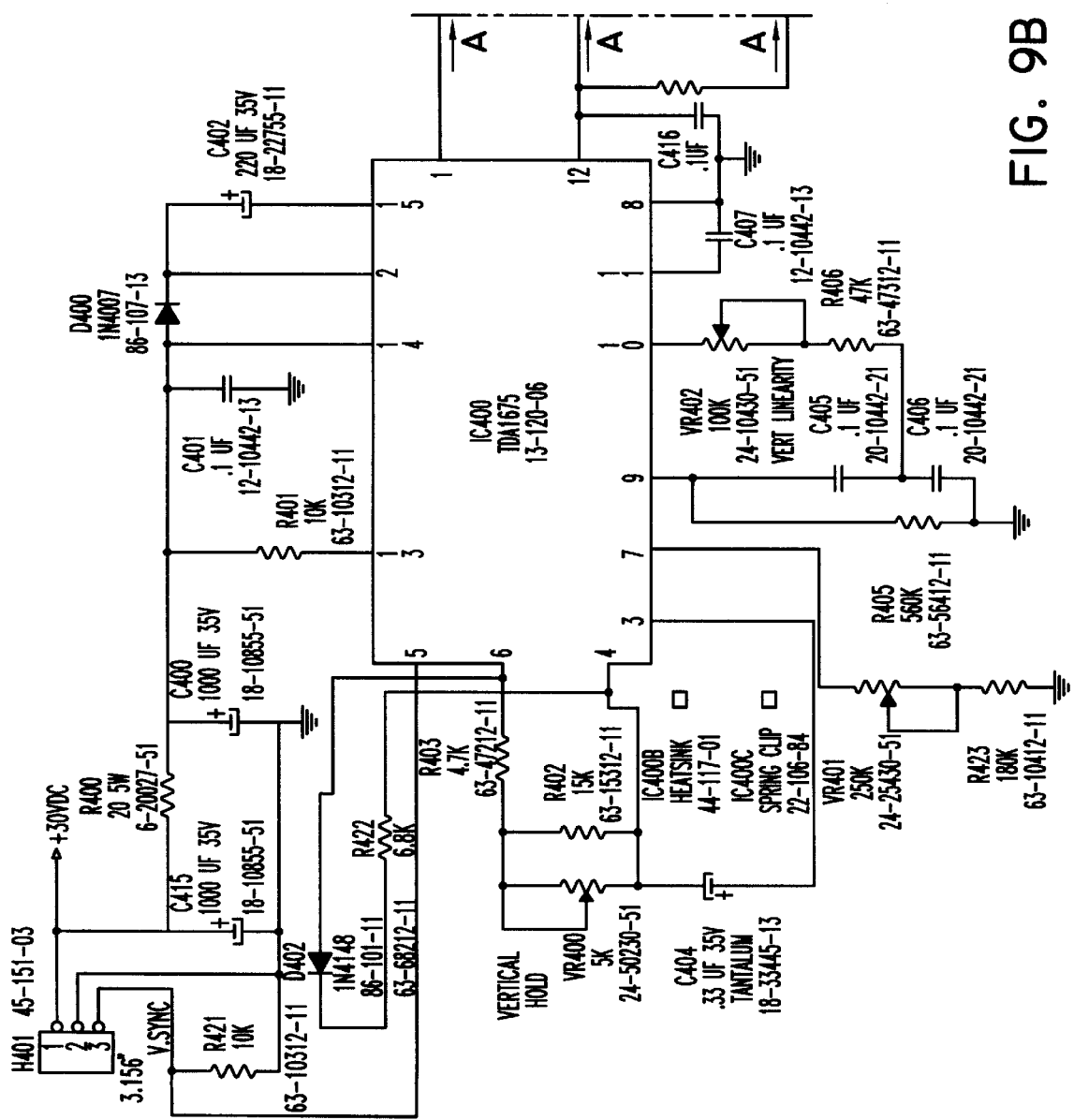
Figure 10A:
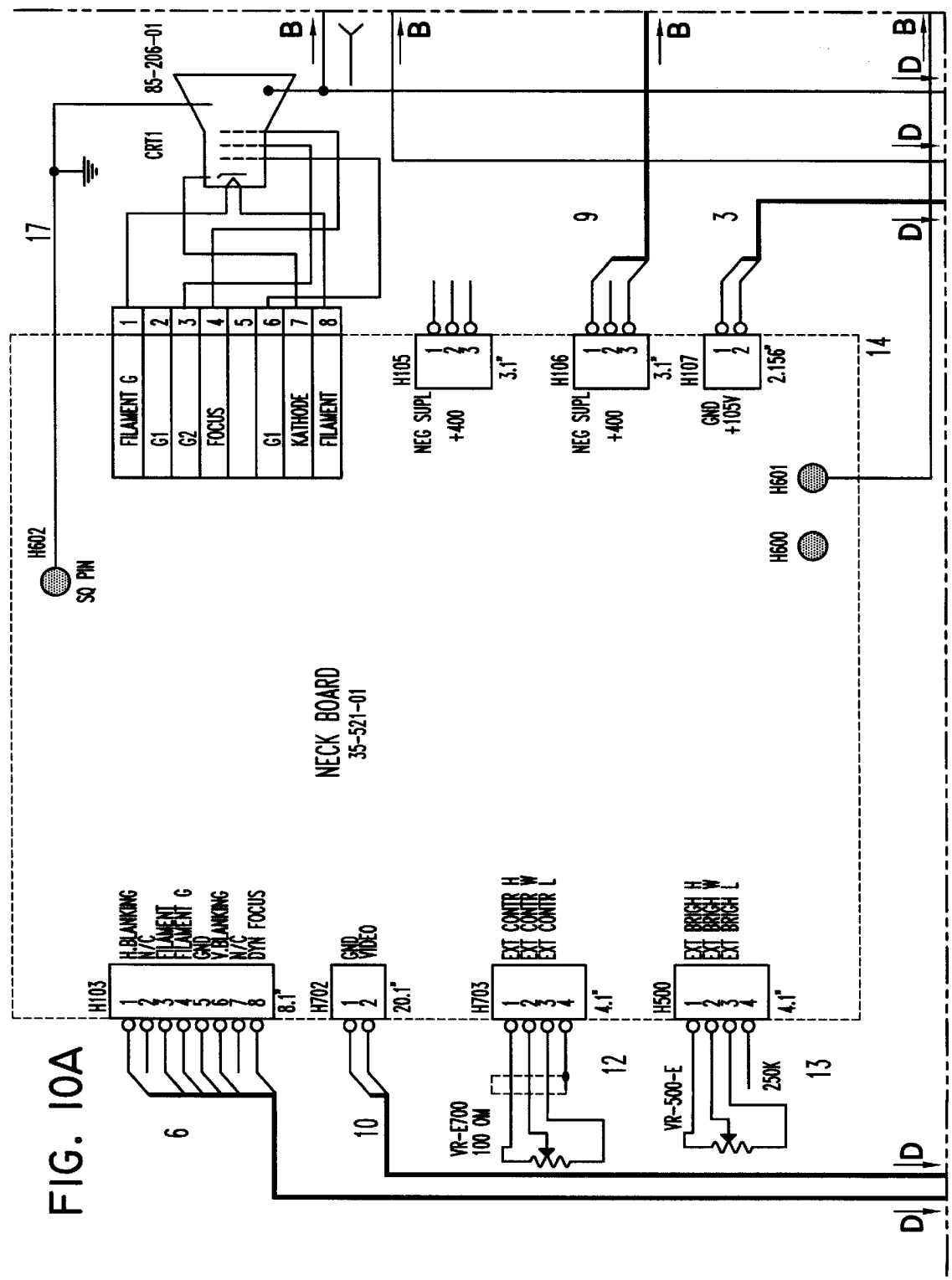
FIGS. 10A–10D, collectively, arranged as shown in FIG. 10, constitute an overall cable diagram of an example of the entire monitor illustrating detailed interconnections.
Figure 10B:
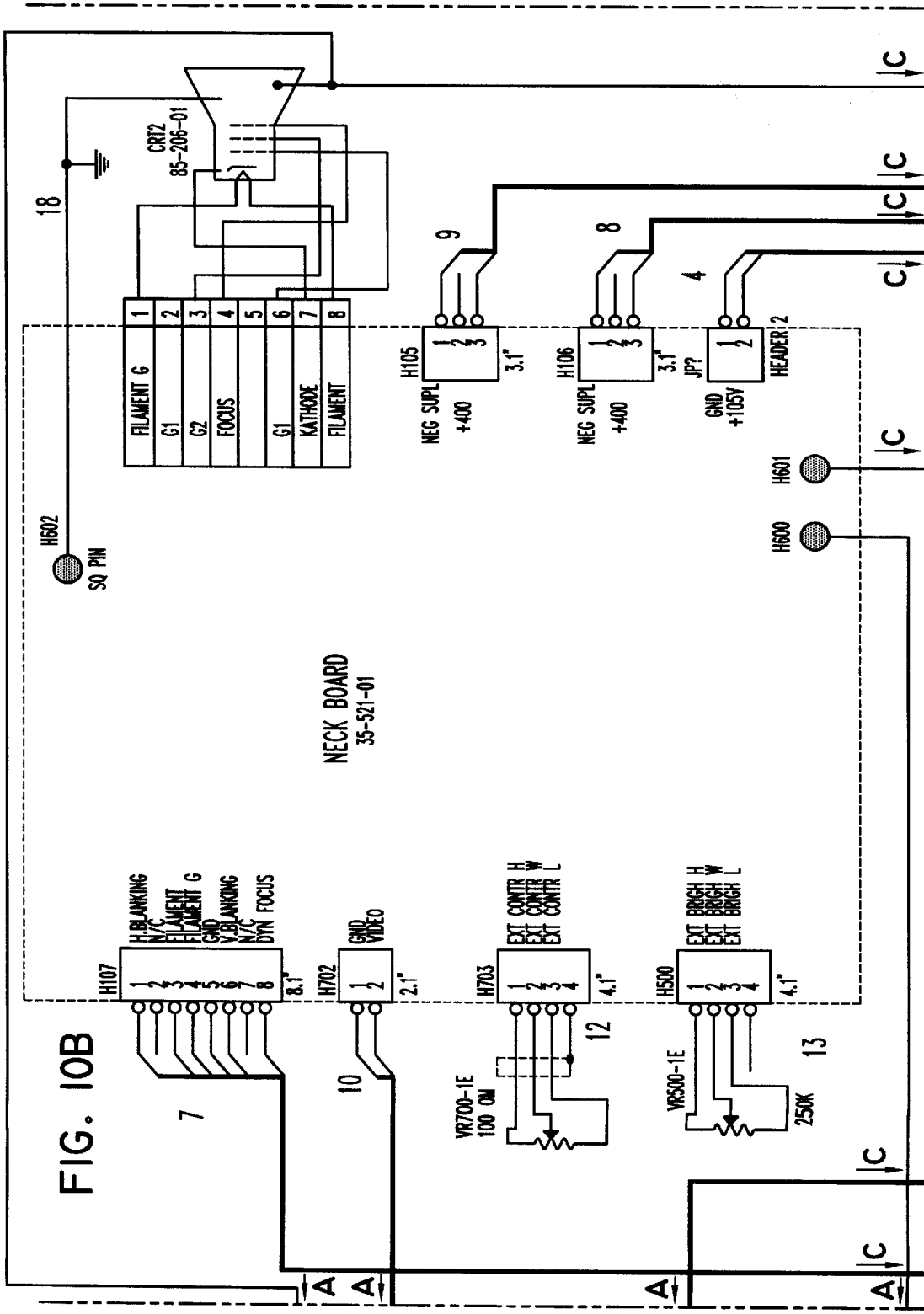
Figure 10C:
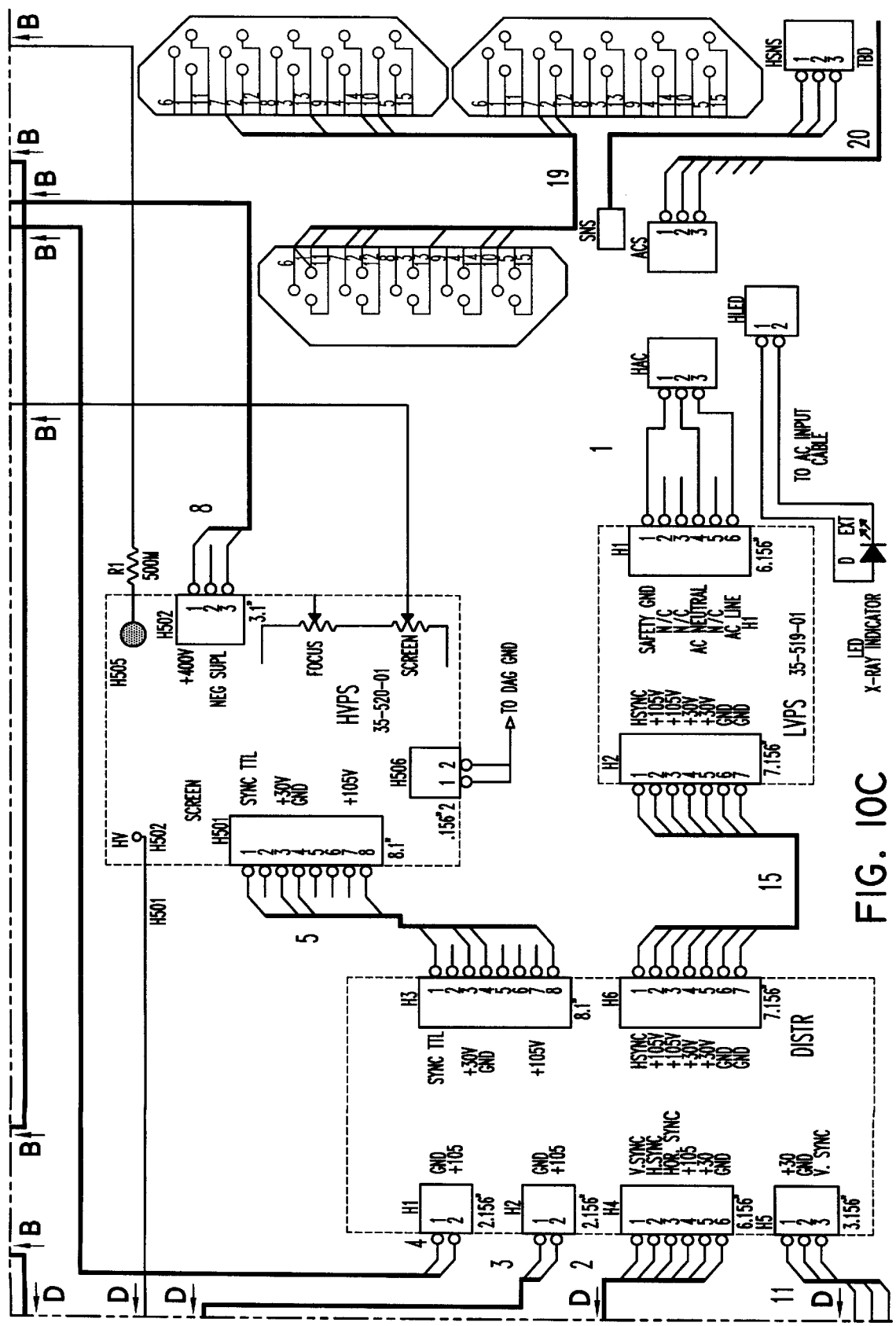
Figure 10D:
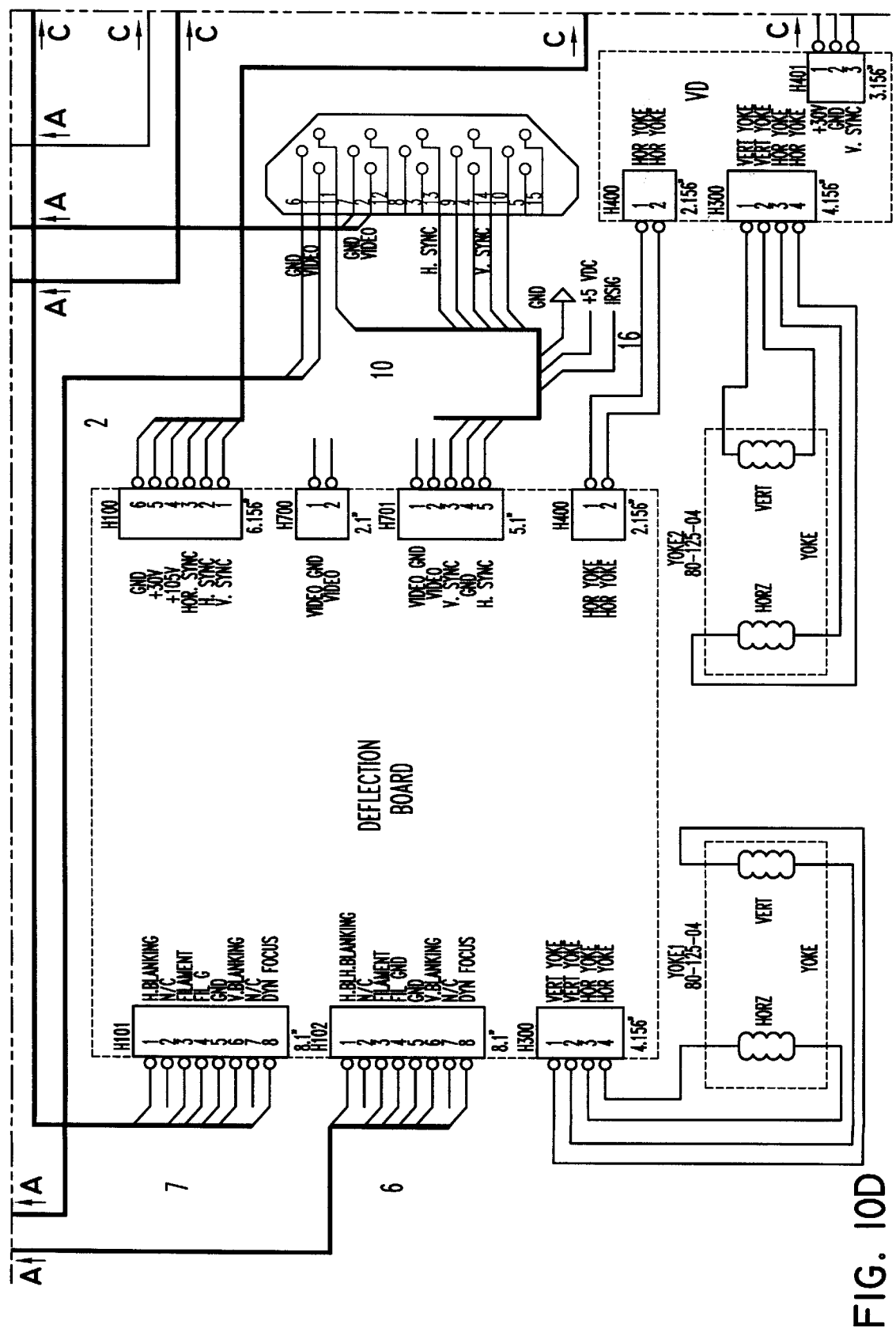

An overall cable diagram is shown in the various parts of FIG. 10. It provides details of the wiring between the deflection boards, the yokes, the CRTs, and the overall monitor wiring interconnections.

The described embodiment of the invention provides a monitor assembly that is modular, has high resolution 15-inch twin displays, and is easily adjustable for the surgeon's viewing of the x-ray output.

A wide variety of additional alternatives are embraced within the scope of the invention in its broader aspects. For instance, the image intensifier employed in the detector may be either of a type that intensifies optical images (as in the above-described "FluoroScan IV" system) or of a type that intensifies x-ray images. Again, in place of an image intensifier and video camera, the detector may be a direct digital 2-dimensional x-ray detector; an example of such a device is the "FlashScan 20" high resolution flat panel device of dpiX, A Xerox Company, which is an amorphous silicon image sensor that acquires conventional x-ray images and converts them to digital form in a way that can provide fluoroscopic imaging in real time.

An alternative embodiment of an x-ray fluoroscopic imaging system in which the present invention can be incorporated is that described in the aforementioned copending U.S. patent application Ser. No. 08/794,615, which describes various alternative embodiments and modifications suitable for such use.

Such an alternative embodiment of the x-ray fluoroscopic imaging system which can be used to measure bone mineral density (BMD) in, for example, the forearm, wrist, ankle or heel of a human patient will be described with reference to FIG. 13. This imaging system 200 is also entirely contained in a wheeled cart or cabinet 210 that can easily be rolled from place to place. The cabinet includes a generally rectangular, upright body 212 that supports a monitor 214 having two displays (only one being shown) on its top surface and has, in its upper portion, a keyboard 216 and an articulated member 218; the cabinet also contains a computer (not shown) for processing data as hereinafter further discussed. The two displays, with their mounting and circuitry, may incorporate features of the present invention.

The outer end of articulated member 218 carries a mini C-arm 220 having an x-ray source 222 and a detector 224 respectively fixedly mounted at its opposite extremities so that an x-ray beam 226 from source 222 impinges on the input end 228 of the detector, the source and detector being spaced apart by the C-arm sufficiently to define a gap 229 between them, in which the limb or extremity of a human patient 230 can be inserted in the path of the x-ray beam 226. The C-arm is connected to the end of member 218 by a 3-way pivotal mounting 232 that enables the C-arm to be swivelled or rotated through 360° in each of three mutually perpendicular (x, y, z) planes and to be held stably at any desired position, while the member 218 is itself mounted and jointed to enable its outer end and the C-arm to be angularly displaced both horizontally and vertically. The multidirectional angular movability of the mini C-arm facilitates the positioning of the source and detector in relation to a patient body portion to be irradiated.

Preferably, either the x-ray source or the x-ray detector includes a control panel 250 that is coupled to the imaging system computer to provide a physician with easy access within the sterile field to predefined imaging control functions associated with the x-ray fluoroscopic imaging system. The control panel 250 is illustrated in FIG. 13 as being mounted on the detector 224. Preferably, the control panel 250, like the panel 50 of FIG. 8, includes an array of membrane switches, each of which is provided to activate at least one function performed by the x-ray fluoroscopic imaging system. In one embodiment, each switch in the array has a raised button profile which provides tactile feedback, completes a signal circuit when contact material mounted on the underside of the raised button profile which provides tactile feedback is depressed to a base layer and breaks the signal circuit when pressure on the contact material is released.

The beam 226 emitted by the x-ray source 222 is a cone-shaped beam (i.e. a volume beam as opposed to a pencil beam or fan beam) that impinges on a flat x-ray-sensitive receiving surface of the detector 224 at or adjacent the detector input end; this receiving surface faces the source across the gap 229 and is perpendicular to the axis of the beam path, so that the intersection of the receiving surface and the conical x-ray beam is an extended circular (2-dimensional) area. The term "field of view" is used herein to refer to the latter circular area, or that portion of it to which the detector responds, and also to designate the region, within the beam path or gap 229, the contents of which will be imaged by the detector. It will be understood that the area of the field of view as measured in a plane transverse to the beam path axis is sufficient to encompass objects of the size desired to be imaged or otherwise studied, e.g. a human wrist or heel.

The receiving surface of the detector 224 is a surface of an x-ray-to-visible-light converter, such as a layer of phosphor or scintillator material covered externally by a light shield, that converts impinging x-rays to visible light. The detector may include a Cesium Iodide vacuum tube image intensifier or an image intensifier of the high-gain microchannel plate type, and a planar output surface on which is produced an output visible-light image of the field of view, in accordance with well-known principles of fluoroscopic imaging. The combined converter and image intensifier elements of the detector 224 may be as described in the aforementioned U.S. Pat. No. 4,142,101 which is incorporated herein by reference.

In addition, the detector assembly includes a video camera (not separately shown) for viewing the image on the aforementioned planar output surface and producing a signal output representative of that viewed image. The video camera can be a television camera and can operate according to a video standard such as NTSC or CCIR. When the system is employed for fluoroscopic imaging, the signal output of the video camera is processed by the onboard computer to produce video images on one or both monitors 214; the system also includes devices for recording and, optionally, printing out these video fluoroscopic images.

As thus far described, the system 200 is essentially identical to currently available mini C-arm x-ray fluoroscopic imaging systems, e.g. having specifications as set forth above for the system 10 of FIG. 1.

A power supply for the x-ray source, and instrumentalities for controlling or varying current (mA) and voltage (kV), not shown, are incorporated in the system as well.

Since the detector in the fluoroscopic imaging system detects x-ray emission from a cone-beam source over an extended two-dimensional area (the cross-section of the x-ray beam path in the plane of the detector receiving surface), there is inherent variation (i.e., variation attributable to the source and/or the detector having the image intensifier, independent of attenuation by any object interposed in the beam path) in received radiation intensity over the field of view. The image data obtained for the wrist and calibration bone sample by the steps described above are corrected for this inherent variation in order to enable more accurate calculation of BMD.

The calculation of data to produce BMD measurements could be performed with an onboard computer in a mini C-arm fluoroscopic system such as the "FluoroScan III" system, or in another computer. The functions of data acquisition/storage and BMD computation therefrom could be performed by different computers. Also, instead of digitizing the detector output data before conversion to logarithms, the logarithmic conversion could be performed first (e.g. with a log amplifier) and digitized thereafter. Moreover, in addition to or in place of the fixtures described above for holding the body portion stationary, appropriate software could be employed to re-register the images if there is movement.

A more detailed description of this embodiment and its operation is provided in the aforementioned U.S. application Ser. No. 08/794,615 which is incorporated herein by reference.

It is to be understood that the invention is not limited to the procedures and embodiments hereinabove specifically set forth, but may be carried out in other ways without departure from its spirit.

What is claimed is:

1. An x-ray fluoroscopic imaging system comprising:
   a portable cabinet;
   a video monitor including two displays;
   a support arm assembly;
   an articulated arm assembly having at least one movable arm and connecting said support arm assembly to said portable cabinet; and
   a C-arm assembly having a C-arm carried by said support arm assembly, an x-ray source assembly including an x-ray source and an x-ray detector assembly including an image receptor located at opposing locations on the C-arm such that said x-ray source and image receptor face each other so that x-rays emitted by said x-ray source impinge on said image receptor;
   wherein the improvement comprises:
   a single driver interface for the two displays for 100% synchronous operation of both displays to display images required by the fluoroscopic imaging system.

2. A system as defined in claim 1, wherein the monitor has two SVGA multiscan CRTs.

3. A system as defined in claim 2, wherein the two displays have individual yokes, video processor PCBs, and power supplies.

4. A system as defined in claim 2, wherein the monitor comprises two displays with IR sensor window for IR control.

5. A system as defined in claim 1, including a single rotatable enclosure mounting the two displays to display images required by the fluoroscopic imaging system.

6. A system as defined in claim 5, wherein the displays are two SVGA multiscan CRTs, wherein the monitor comprises two displays with IR sensor window for IR control, wherein the two displays have individual yokes, video processor PCBs, and power supplies, wherein the rotatable enclosure is disposed on the portable cabinet, and wherein the rotatable enclosure provides rotation of about 40°.

* * * * *